US009872801B2

(12) United States Patent
Hammons et al.

(10) Patent No.: US 9,872,801 B2
(45) Date of Patent: Jan. 23, 2018

(54) ZONED TOPSHEET

(71) Applicant: The Procter & Gamble Company, Cincinnati, OH (US)

(72) Inventors: John Lee Hammons, Hamilton, OH (US); Jody Lynn Hoying, Maineville, OH (US); Luisa Valerio Gonzalez, Oakley, OH (US); Sybille Fuchs, Frankfurt (DE)

(73) Assignee: The Procter & Gamble Company, Cincinnati, OH (US)

( * ) Notice: Subject to any disclaimer, the term of this patent is extended or adjusted under 35 U.S.C. 154(b) by 1147 days.

(21) Appl. No.: 14/034,589

(22) Filed: Sep. 24, 2013

(65) Prior Publication Data
US 2014/0296809 A1    Oct. 2, 2014

Related U.S. Application Data

(63) Continuation of application No. 12/188,527, filed on Aug. 8, 2008, now abandoned.

(51) Int. Cl.
*A61F 13/513*    (2006.01)
*A61F 13/475*    (2006.01)
(Continued)

(52) U.S. Cl.
CPC .......... *A61F 13/513* (2013.01); *A61F 13/476* (2013.01); *A61F 13/4751* (2013.01);
(Continued)

(58) Field of Classification Search
USPC ......... 604/365; 264/468, 129, 154; 428/131, 428/137, 138
See application file for complete search history.

(56) References Cited

U.S. PATENT DOCUMENTS 5,180,620 A    1/1993 Mende
5,533,991 A    7/1996 Kirby
(Continued)

FOREIGN PATENT DOCUMENTS

FR    2 713 083    6/1995
JP    2004/298454    10/2004
WO    WO 2006/009995    1/2006

OTHER PUBLICATIONS

PCT International Search Report, dated Nov. 23, 2009, 7 pages.

*Primary Examiner* — Lynda Salvatore
(74) *Attorney, Agent, or Firm* — Brian M. Bolam; Dara M. Kendall; Andrew J. Hagerty

(57) ABSTRACT

An absorbent article having a topsheet, a backsheet, and an absorbent core between the topsheet and backsheet. The topsheet has a central region, a first end intermediate region, a first end region, a second end intermediate region, a second end region, an edge region, and an intermediate edge region. The central region, first end intermediate region, first end region, second end intermediate region, and second end region are disposed on a line generally parallel to the longitudinal centerline. The central region, intermediate edge region, and edge region are disposed on a line generally parallel to the transverse centerline. The central region texture, first end intermediate region texture, first end region texture, second end intermediate region texture, and second end region texture differ from one another. The central region texture, intermediate edge region texture, and edge region texture differ from one another.

2 Claims, 24 Drawing Sheets

(51) Int. Cl.
*A61F 13/476* (2006.01)
*A61F 13/512* (2006.01)

(52) U.S. Cl.
CPC ...... *A61F 13/512* (2013.01); *A61F 13/51305* (2013.01); *A61F 2013/51338* (2013.01); *A61F 2013/51344* (2013.01); *A61F 2013/51383* (2013.01); *Y10T 428/2395* (2015.04); *Y10T 428/23929* (2015.04); *Y10T 428/24273* (2015.01); *Y10T 428/24479* (2015.01); *Y10T 428/24777* (2015.01)

(56) References Cited

U.S. PATENT DOCUMENTS

| | | | |
|---|---|---|---|
| 5,658,639 A * | 8/1997 | Curro | A61F 13/00991 427/243 |
| 5,743,776 A | 4/1998 | Igaue et al. | |
| 5,792,404 A | 8/1998 | Cree | |
| 5,795,921 A | 8/1998 | Dyer et al. | |
| 5,849,805 A | 12/1998 | Dyer | |
| 5,873,869 A | 2/1999 | Hammons et al. | |
| 5,899,893 A | 5/1999 | Dyer et al. | |
| 5,989,478 A * | 11/1999 | Ouellette | A61F 13/15731 264/129 |
| 6,025,049 A | 2/2000 | Ouellette et al. | |
| 6,117,523 A | 9/2000 | Sugahara | |
| 6,180,052 B1 | 1/2001 | Ouellette et al. | |
| 6,231,948 B1 | 5/2001 | Ouellette et al. | |
| 6,383,431 B1 | 5/2002 | Dobrin | |
| 6,911,574 B1 | 6/2005 | Mizutani | |
| 7,172,801 B2 | 2/2007 | Hoying et al. | |
| 7,410,683 B2 | 8/2008 | Curro et al. | |
| 7,507,459 B2 | 3/2009 | Turner et al. | |
| 7,553,532 B2 | 6/2009 | Turner et al. | |
| 2003/0125687 A1 | 7/2003 | Gubernick | |
| 2004/0127875 A1 | 7/2004 | Hammons et al. | |
| 2004/0229008 A1 | 11/2004 | Hoying | |
| 2004/0265533 A1 * | 12/2004 | Hoying | A61F 13/15707 428/92 |
| 2005/0124951 A1 | 6/2005 | Kudo et al. | |
| 2005/0281976 A1 | 12/2005 | Curro et al. | |
| 2006/0184150 A1 | 8/2006 | Noel | |
| 2006/0286343 A1 | 12/2006 | Curro et al. | |
| 2007/0116926 A1 | 5/2007 | Hoying et al. | |
| 2008/0119807 A1 | 5/2008 | Curro et al. | |
| 2008/0154226 A9 | 6/2008 | Hammons | |
| 2009/0030390 A1 | 1/2009 | Hammons | |
| 2009/0030391 A1 | 1/2009 | Hammons | |
| 2009/0157030 A1 | 6/2009 | Turner et al. | |
| 2009/0209930 A1 | 8/2009 | Hammons et al. | |
| 2010/0004615 A1 | 1/2010 | Boissier | |
| 2011/0106036 A1 | 5/2011 | Stähl et al. | |

* cited by examiner

ZONED TOPSHEET

FIELD OF THE INVENTION

The present invention relates to a topsheet for an absorbent article.

BACKGROUND OF THE INVENTION

Absorbent articles, such as sanitary napkins, diapers, adult incontinence products, and the like, are designed to be worn in close proximity to the crotch of the wearer. Absorbent articles need to provide for fluid acquisition and retention and need to be comfortable to wear.

In use, absorbent articles are stressed by a variety of fluid handling demands. For instance, the central portion of the pad may be assaulted with fluid flow that may either be a trickle or a gush of fluid. If the wearer is lying down on her front or back, fluid may have a tendency to run off of the front end or rear portion of the absorbent article. Typical absorbent articles are approximately the same width as the crotch of the wearer, which can be somewhat narrow. Thus, there is potential for fluid to run off the sides of the absorbent article and soil the wings of the absorbent article, if present, or soil the wearer's undergarment and/or clothing.

A woman's crotch region can comprise many different types of tissues. For instance, the pubic area, labia majora, inner thigh, and anus can each have a different skin texture. Sanitary napkins commonly cover the labia, portions of the crotch forward of the labia, portions of the crotch rearward of the labia, and portions of the crotch laterally adjacent the labia. As a woman wearing a sanitary napkin moves, portions of the sanitary napkin can rub up against nearby body surfaces. Given the complex geometry of a woman's crotch region and the dynamic geometry of a woman's crotch as she moves, different portions of the woman's crotch are exposed to different rubbing forces and the friction between the sanitary napkin and wearer's crotch can vary depending on the location.

The moisture and chemical environments of a woman's crotch can also vary as a function of location. For instance, the labia majora may be exposed to menses and/or urine. The medial portion of the woman's pubic area may be exposed to perspiration. Portions adjacent the medial area may be subjected to more moisture due to the lack of hair and the tendency for a woman's panty to closely conform to the junction of the inner thigh and the crotch and pubic area. The area near the anus may be exposed to more perspiration and anal leakage than areas further away from the anus.

Given the variety of fluid handling demands placed on different portions of an absorbent article, the different physical interactions between portions of an absorbent article and portions of a wearer's body, and different moisture and chemical environments of different portions of a wearer's crotch region, there is continuing and unaddressed need for absorbent articles having a topsheet that has different textures that are arranged to provide fluid handling benefits where needed, skin comfort benefits where needed, and in regions of the topsheet where fluid handling benefits and skin comfort benefits are both desired, a texture is provided that can be acceptable for meeting both needs.

SUMMARY OF THE INVENTION

An absorbent article comprising a topsheet, a backsheet and an absorbent core between the topsheet and the backsheet is disclosed. The topsheet can have a longitudinal centerline and transverse centerline, wherein the topsheet comprises a central region, a first end intermediate region, a first end region, a second end intermediate region, a second end region, an edge region, and an intermediate edge region. The central region, the first end intermediate region, the first end region, the second end intermediate region, and the second end region can be disposed on a line generally parallel to the longitudinal centerline. The central region, the intermediate edge region, and the edge region can be disposed on a line generally parallel to the transverse centerline. The central region can be between the first end region and the second end region. The first end intermediate region can be between the central region and the first end region. The second end intermediate region can be between the central region and the second end region. The central region can have a central region body facing surface having a central region texture. The first end intermediate region can have a first end intermediate region body facing surface having a first end intermediate region texture. The first end region can have a first end region body facing surface having a first end region texture. The second end intermediate region can have a second end intermediate region body facing surface having a second end intermediate region texture. The second end region can have a second end region body facing surface having a second end region texture. The intermediate edge region can have an intermediate edge region body facing surface having an intermediate edge region texture. The edge region can have an edge region body facing surface having an edge region texture. The central region texture, the first end intermediate region texture, the first end region texture, the second end intermediate region texture, the second end region texture can differ from one another. The central region texture, the intermediate edge region texture, and the edge region texture can differ from one another.

DETAILED DESCRIPTION OF THE INVENTION

Figure 1:
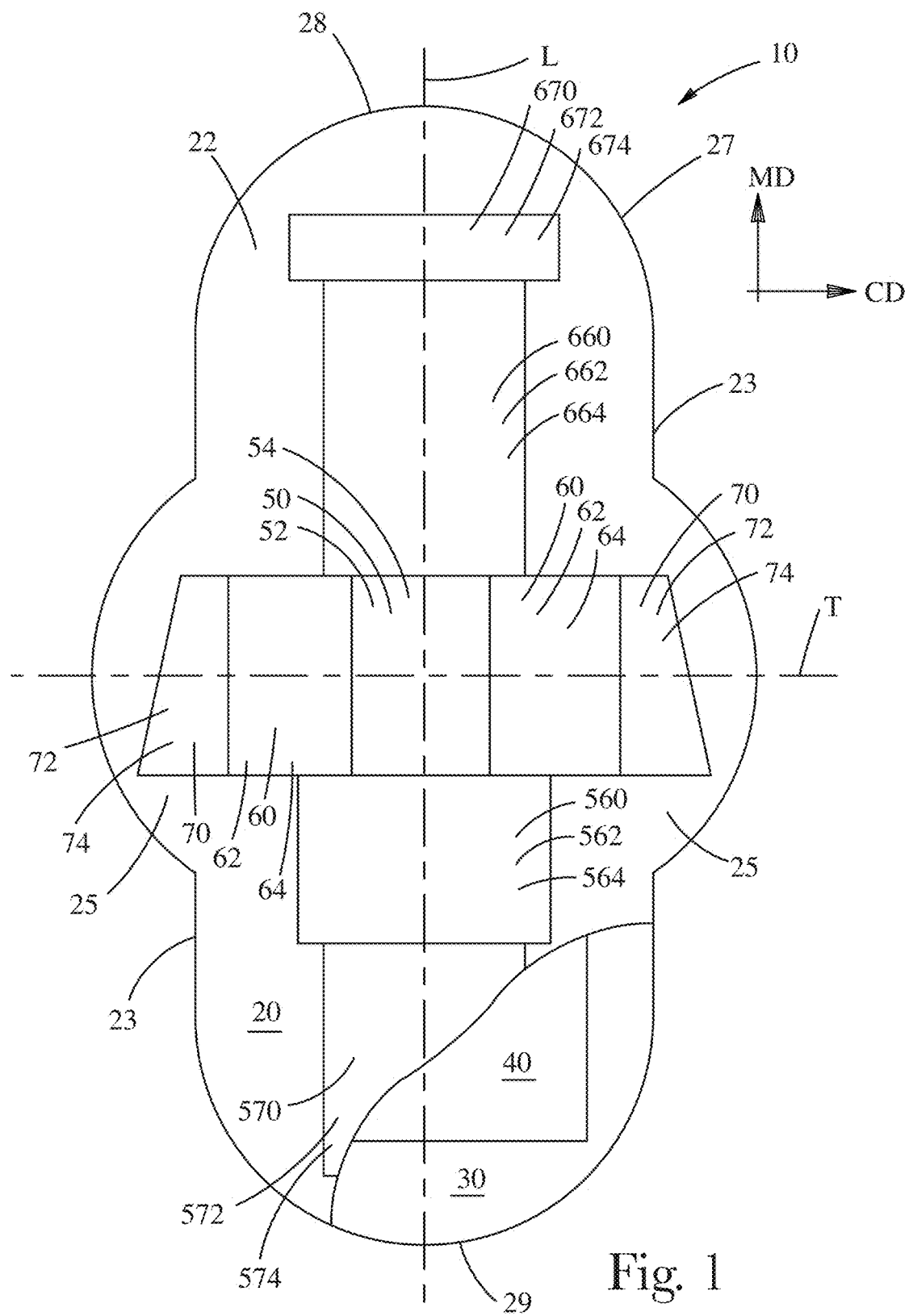
FIG. 1 is a schematic of a top view of a sanitary napkin.

FIG. 1 is an illustration of an embodiment of an absorbent article 10 providing for different skin health benefits and fluid acquisition benefits for different portions of the wearer's crotch. The absorbent article 10 can comprise a liquid pervious topsheet 20, a fluid impervious backsheet 30, and an absorbent core 40 disposed between the topsheet 20 and backsheet 30. The topsheet 20 can be described as being in a facing relationship with the absorbent core 40. The absorbent article can be selected from the group consisting of an incontinence product, a sanitary napkin, and a diaper.

The absorbent core can be comprised of cellulosic material, such as Foley Fluff, available from Buckey Technologies, Inc., Memphis, Tenn., that is disintegrated and formed into a core having a density of about 0.07 grams per cubic centimeter and a caliper of about 10 mm. The absorbent core 40 can be a high internal phase emulsion foam or a polyacrylate material.

The absorbent article 10 is discussed herein in the context of what is commonly referred to in the art as a sanitary napkin, menstrual pad, or catamenial pad. It is to be understood that the absorbent article 10 can be any absorbent article designed to be worn in proximity with the crotch of the wearer.

The absorbent article 10 and each layer or component thereof can be described as having a body facing surface and a garment facing surface. As can be understood by considering the ultimate use for absorbent articles, such as sanitary napkins, diapers, incontinent products and the like, the body facing surfaces are the surfaces of the layers or components that are oriented closer to the body when in use, and the garment facing surfaces are the surfaces that are oriented closer to the undergarment of the wearer when in use. Therefore, for example, the topsheet 20 has a body facing surface 22 (that can actually be a body contacting surface) and a garment facing surface opposing the body facing surface 22. The garment facing surface of the backsheet 30, for example, can be oriented closest to, and can contact the wearer's panties in use.

The topsheet 20 can comprise a central region 50, a first end intermediate region 660, a first end region 670, a second end intermediate region 560, a second end region 570, an edge region 70, and an intermediate edge region 60. The central region 50, first end intermediate region 660, first end region 670, second end intermediate region 560, and second end region 570 can be disposed on a line generally parallel to the longitudinal centerline L.

The central region 50, intermediate edge region 60, and edge region 70 can be disposed on a line generally parallel to the transverse centerline T.

The central region 50 is between the first end region 670 and the second end region 570. The first end intermediate region 660 is between the central region 50 and the first end region 670. The second end intermediate region 560 is between the central region 50 and the second end region 570.

In the arrangement described above, starting from the intersection of the longitudinal centerline L and the transverse centerline T and moving on a line generally parallel to the transverse centerline T, the various regions can be arranged in the order of the central region 50, the intermediate edge region 60, and the edge region 70. Starting from the intersection of the longitudinal centerline L and the transverse centerline T and moving on a line generally parallel to the longitudinal centerline L towards the first end edge 28, the various regions can be arranged in the order of the central region 50, the first end intermediate region 660, and the first end region 670. Starting from the intersection of the longitudinal centerline L and the transverse centerline T and moving on a line generally parallel to the longitudinal centerline L towards the second end edge 29 of the absorbent article 10, which opposes the first end edge 28, the end edges being generally located at the edges of the absorbent article 10 on the longitudinal centerline L, the various regions can be arranged in the order of the central region 50, the second end intermediate region 560, and the second end region 570. At least a portion of the central region 50 can be on the longitudinal centerline L. At least a portion of the central region 50 can be on the longitudinal centerline L and transverse centerline T.

Longitudinal centerline L and transverse centerline T, the longitudinal centerline L and transverse centerline T being orthogonal to one another, define a two-dimensional plane of the absorbent article 10 prior to use, which, in the embodiment shown is associated with the machine direction (MD) and cross machine direction (CD) as is commonly known in the art of making absorbent articles using high-speed commercial production lines. The absorbent article 10 has a length, which is the longest dimension measured parallel to the longitudinal axis L. The article 10 has a width, which is the dimension measured in the CD, e.g., parallel to the transverse centerline T. The width can vary or be substantially constant along the length of the sanitary napkin. In general, the width can be measured between lateral side edges 23 parallel to the transverse centerline T. The lateral side edges 23 are generally aligned in the longitudinal direction and may be straight, curved, or combinations of straight and curved sections.

As illustrated in FIG. 1, the central region 50, intermediate edge region 60, and edge region 70 can be disposed on a line generally parallel to the transverse centerline T. The central region 50, intermediate edge region 60, and edge region 70 can be disposed on a line that is no more than about thirty degrees out of alignment with the transverse centerline T.

As used herein, the word "region" refers to an area set off as distinct from surrounding or adjoining areas. Thus, for example, a topsheet comprising uniformly spaced apertures, each of which are the same size, over the entire surface of the topsheet cannot be considered to have any regions. Moreover, for example, in a topsheet comprising uniformly spaced apertures, each of which are the same size, a single aperture and locally surrounding material cannot be considered a region because that single aperture and locally surrounding material are not distinct from surrounding or adjoining areas. Similarly, for example, a topsheet comprising uniformly spaced elements, each element being the same, over the entire surface of the topsheet cannot be considered to have any regions. Nor, in a topsheet comprising uniformly spaced elements, for example, may a single element and locally surrounding material be considered a region. Regions can be separated from one another such that there is an absence of like structured material between the regions. A region can comprise an area more than about the product of 5% of the length of the absorbent article and 5% of the width of the absorbent article, the width being measured at the centroid of the respective region (i.e. the particular region of interest: the central region 50, first end intermediate region 660, first end region 670, second end intermediate region 560, second end region 570, intermediate edge region 60, and edge region 70).

Individually, any of the central region 50, edge region 70, and intermediate edge region 60 can constitute more than about 5% the width of the absorbent article 10 as measured between the lateral side edges 23 at the location of the centroid of the region. Individually, any of the central region 50, edge region 70, and intermediate edge region 60 can constitute more than about 10% the width of the absorbent article 10 as measured between the lateral side edges 23 at the location of the centroid of the region. Individually, any of the central region 50, edge region 70, and intermediate edge region 60 can constitute more than about 20% the width of the absorbent article 10 as measured between the side edges 23 at the location of the centroid of the region. Thus, in one example embodiment, the central region 50 can constitute about 30% of the width of the absorbent article, the intermediate edge region 60 can constitute about 10% of the width of the absorbent article, and the edge region 70 can constitute about 15% of the width of the absorbent article.

The central region 50 has a central region body facing surface 52. The central region body facing surface 52 has a central region texture 54. The first end intermediate region 660 has a first end intermediate region body facing surface 662. The first end intermediate region body facing surface 662 has a first end intermediate region texture 664. The first end region 670 has a first end region body facing surface 672. The first end region body facing surface 672 has a first end region texture 674. The second end intermediate region 560 has a second end intermediate region body facing surface 562. The second end intermediate region body facing surface 562 has a second end intermediate region texture 564. The second end region 570 has a second end region body facing surface 572. The second end region body facing surface 572 has a second end region texture 574. The intermediate edge region 60 has an intermediate edge region body facing surface 62. The intermediate edge region body facing surface 62 has an intermediate edge region texture 64. The edge region 70 has an edge region body facing surface 72. The edge region body facing surface 72 has an edge region texture 74. The central region texture 54, first end intermediate region texture 664, first end region texture 674, second end intermediate region texture 564, second end region texture 574, intermediate edge region texture 64, and edge region texture 74 can be designed to provide particular benefits with respect to fluid handling and/or comfort.

As used herein, texture refers to the topography of the relevant material in directions orthogonal to a plane defined by the longitudinal centerline L and transverse centerline T. The topography of a material can be provided, for example, by portions of material that are higher or lower relative to adjacent portions of material, holes through the material, and portions of the material in which the structure of the material is plastically disrupted or disturbed relative to adjacent portion. Topography can be characterized at a resolution of about 100 microns over an area of at least about four square millimeters.

For some absorbent articles 10, embodiments are contemplated in which channels, indentations, dimples, and/or embossments may not be considered to provide for texture of any of the central region 50, first end intermediate region 660, first end region 670, second end intermediate region 560, second end region 570, intermediate edge region 60, and edge region 70. For such designs, texture for the regions can be provided by structures other than channels, indentations, dimples, and/or embossments. As used herein, a "channel" is an indentation having an in-plane length greater than the width, the length being the longest dimension, curved or straight, within the indentation and the in-plane width being the shortest dimension of the indentation. An indentation, dimple, or embossment can be considered to be a structure created by compressing portions of the absorbent article.

The central region texture 54, first end intermediate region texture 664, first end region texture 674, second end intermediate region texture 564, and second end region texture 574 can differ from one another. The central region texture 54, intermediate edge region texture 64, and edge region texture 74 can differ from one another. Arranged in this manner, the central region texture 54, first end intermediate region texture 664, first end region texture 674, second end intermediate region texture 564, and second end region texture 574 can differ from one another to provide for different fluid handling and/or comfort benefits in different locations of the body facing surface of the topsheet 20. Further, arranging the central region texture 54, intermediate edge region texture 64, and edge region texture 74 in this manner can also provide for different fluid handling and/or comfort benefits in different locations of the body facing surface of the topsheet 20.

In the embodiment shown in FIG. 1, the central region texture 54 can be designed to provide for a region of the topsheet 20 that can rapidly acquire and retain fluid. One or more of the first end intermediate region texture 664, second end intermediate region texture 564, and the intermediate edge region texture 64 can be designed to be soft so that the topsheet 20 is not irritating to the wearer's labia when the absorbent article 10 is worn and to provide for resistance to flow on the interface between the wearer's body and the topsheet 20 so as to reduce the potential for fluid to escape from being collected by the absorbent article 10 by leaking towards or off the periphery 27 of the absorbent article 10.

The edge region texture 74 can be designed to be comfortable to skin between the labia and inner thigh of the wearer and provide for resistance to lateral fluid flow on the body facing surface of the topsheet 20. The edge region texture 74 can be designed to provide for a soft surface that might come into contact with the wearer's inner thigh if the absorbent article 10 has flaps 25 that are to be folded about the edges of the wearer's panty and to provide for resistance to lateral fluid flow on the surface of the topsheet 20 that can cause soiling of the wearer's skin, undergarment, or clothing.

The first end region texture 674 and second end region texture 574 can be designed to be comfortable to skin in the pubic area or anal region of the wearer and to provide for resistance to fluid flow on the interface between the wearer's body and the topsheet 20 of the absorbent article 10. Leakage of fluid off of the topsheet by a pathway towards the first end edge 28, which may be the front of the absorbent article 10, and/or second end edge 29, which may be the rear of the absorbent article 10 can be a problem when the wearer of the absorbent article 10 is lying on her front or back, as might occur when she is sleeping. One or both of the first end region texture 674 and second end region texture 574 can be designed to provide for fluid acquisition from the wearer's anal region, as might occur from a wearer having anal leakage.

The central region 50, first end intermediate region 660, first end region 670, second end intermediate region 560, and second end region 570, can be disposed on a line generally parallel to the longitudinal centerline L. The central region 50, first end intermediate region 660, first end region 670, second end intermediate region 560, and second end region 570 can be disposed on a line that is no more than about thirty degrees out of alignment with the longitudinal centerline L. Individually, any of the central region 50, first end intermediate region 660, first end region 670, second end intermediate region 560, and second end region 570 can constitute more than about 5%, or more than about 10%, the length of the absorbent article 10 as measured along the longitudinal axis L. Thus, in one example embodiment, the central region 50 can constitute about 30% of the length of the absorbent article 10, the first end intermediate region 660 can constitute about 10% of the length of the absorbent article 10, the first end region 670 can constitute about 10% of the length of the absorbent article 10, the second end intermediate region 560 can constitute about 10% of the length of the absorbent article 10, and the second end region 570 can constitute about 10% of the length of the absorbent article 10.

Individually each of the central region 50, first end intermediate region 660, first end region 670, second end intermediate region 560, second end region 570, intermediate edge region 60, and edge region 70 can constitute more than about 10% of the area of the topsheet, area being measured in the plane of the absorbent article defined by the longitudinal centerline L and transverse centerline T. Individually, each of the central region 50, first end intermediate region 660, first end region 670, second end intermediate region 560, second end region 570, intermediate edge region 60, and edge region 70 can constitute more than about 5% of the area of the topsheet. Individually, each of the central region 50, first end intermediate region 660, first end region 670, second end intermediate region 560, second end region 570, intermediate edge region 60, and edge region 70 can constitute more than about 2% of the area of the topsheet.

Figure 2:
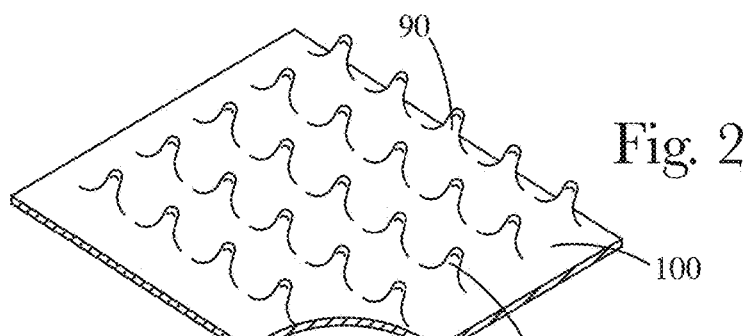
FIG. 2 is schematic of a film having raised portions.
Figure 3:
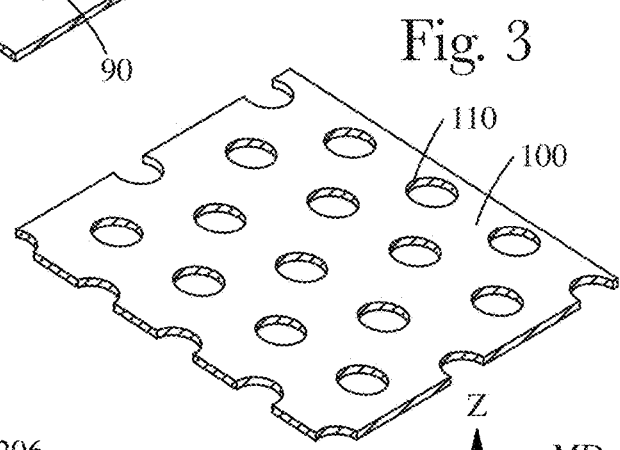
FIG. 3 is schematic of an apertured film.

The central region (50) can comprise a material selected from the group consisting of a film 100 having raised portions 90 (FIG. 2), a film 100 having apertures 110 (FIG. 3), tufted fibers 206 (the tufted fibers forming tufts 209) (FIG. 4), a nonwoven 130, a nonwoven 130 having apertures 110, and a nonwoven 130 having embossments 140 (FIG. 5), and combinations thereof.

The first end intermediate region (660) can comprise a material selected from the group consisting of a film 100 having raised portions 90 (FIG. 2), a film 100 having apertures 110 (FIG. 3), tufted fibers 206 (the tufted fibers forming tufts 209) (FIG. 4), a nonwoven 130, a nonwoven 130 having apertures 110, and a nonwoven 130 having embossments 140 (FIG. 5), and combinations thereof.

The first end region 670 can comprise a material selected from the group consisting of a film 100 having raised portions 90 (FIG. 2), a film 100 having apertures 110 (FIG. 3), tufted fibers 206 (the tufted fibers forming tufts 209) (FIG. 4), a nonwoven 130, a nonwoven 130 having apertures 110, and a nonwoven 130 having embossments 140 (FIG. 5), and combinations thereof.

The second end intermediate region 560 can be selected from the group consisting of a film 100 having raised portions 90 (FIG. 2), a film 100 having apertures 110 (FIG. 3), tufted fibers 206 (the tufted fibers forming tufts 209) (FIG. 4), a nonwoven 130, a nonwoven 130 having apertures 110, and a nonwoven 130 having embossments 140 (FIG. 5), and combinations thereof.

The second end region 570 can comprise a material selected from the group consisting of a film 100 having raised portions 90 (FIG. 2), a film 100 having apertures 110 (FIG. 3), tufted fibers 206 (the tufted fibers forming tufts 209) (FIG. 4), a nonwoven 130, a nonwoven 130 having apertures 110, and a nonwoven 130 having embossments 140 (FIG. 5), and combinations thereof.

The intermediate edge region 60 can comprise a material selected from the group consisting of a film 100 having raised portions 90 (FIG. 2), a film 100 having apertures 110 (FIG. 3), tufted fibers 206 (the tufted fibers forming tufts 209) (FIG. 4), a nonwoven 130, a nonwoven 130 having apertures 110, and a nonwoven 130 having embossments 140 (FIG. 5), and combinations thereof.

The edge region 70 can comprise a material selected from the group consisting of a film 100 having raised portions 90 (FIG. 2), a film 100 having apertures 110 (FIG. 3), tufted fibers 206 (the tufted fibers forming tufts 209) (FIG. 4), a nonwoven 130, a nonwoven 130 having apertures 110, and a nonwoven 130 having embossments 140 (FIG. 5), and combinations thereof.

Figure 6:
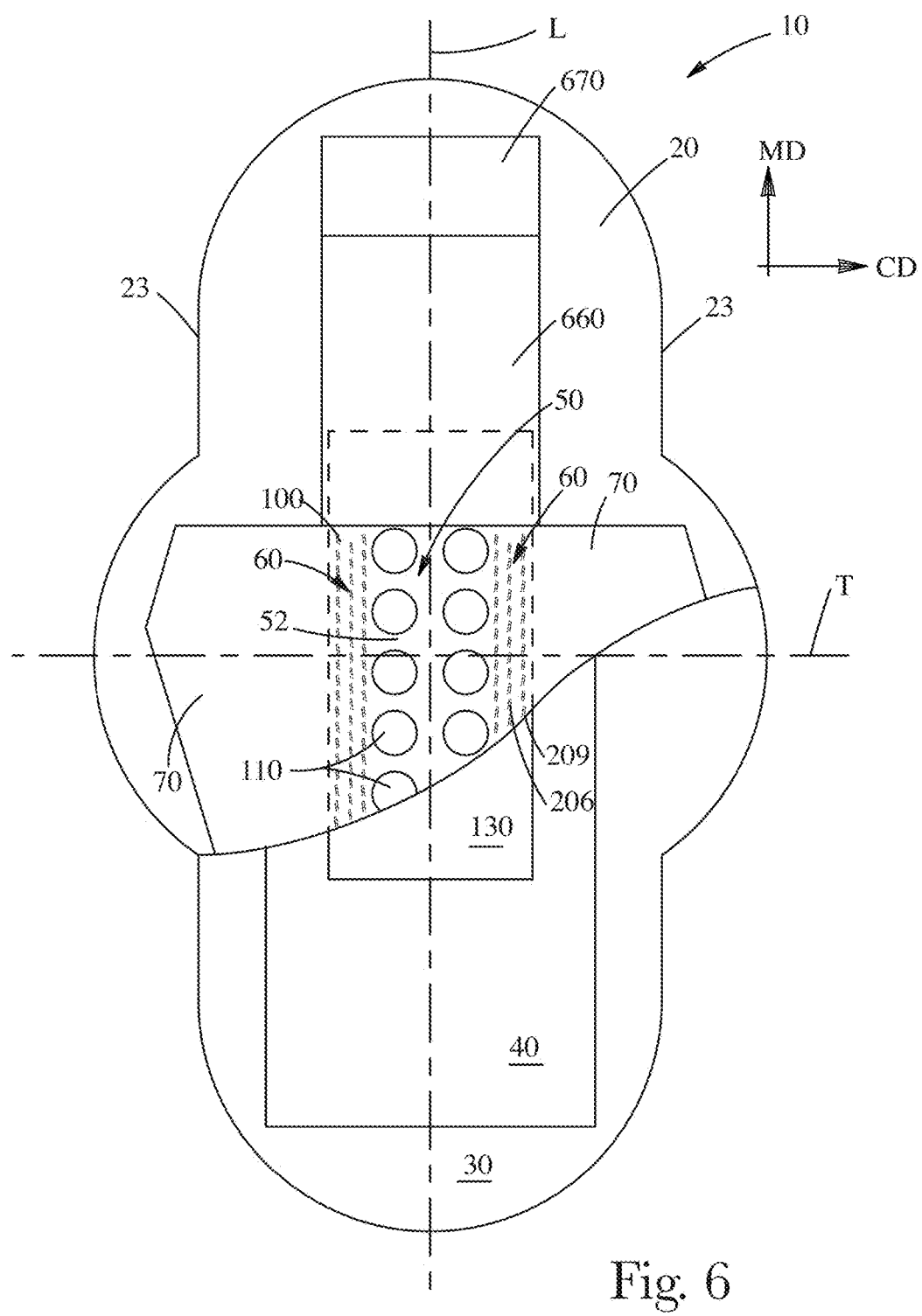
FIG. 6 is a schematic of a top view of a sanitary napkin.

The central region 50 and the intermediate edge region 60 can comprise a film 100 in facing relationship with a nonwoven 130. An example of such an arrangement is illustrated in FIG. 6. Materials that are in a facing relationship can be related such that they are substantially continuously facing, continuously facing, or partially facing. Continuously facing means that at least one entire surface of one material is in effective contact with the other, effective contact being used because even the flattest of surfaces is rough at some scale of measurement. Substantially continuously facing means that the majority of at least one surface of one material is in effective contact with the other material. Partially facing means that more than ten percent of at least one surface of one material is in effective contact with the other material. An overwrap for a cylindrical absorbent core 40 can be considered as being in a facing relationship with the absorbent core 40. The film 100 can be in a substantially continuous, continuous, or partially facing relationship with nonwoven 130. The film 100 in the central region 50 can comprise apertures 110 to provide a pathway for fluid transport through the film 100. In the intermediate edge region 60, tufted fibers 206 (forming tufts 209) from the nonwoven 130 can protrude through the film 100. In embodiments in which tufts 209 protrude through a film 100, the tufts 209 may substantially cover the film 100. For instance, wherein the tufts 209 protrude through the film 100, more than about 50% of the surface of the film 100 can be covered by the tufts. More than about 75% of the surface of the film 100 may be covered by the tufts 209. More than about 90% of the surface of the film 100 may covered by the tufts 209. The film 100 and nonwoven 130 can be arranged such that in the central region 50, the film 100 is the central region body facing surface 52 and the nonwoven 130 is between the film 100 and the absorbent core 40.

Figure 7:
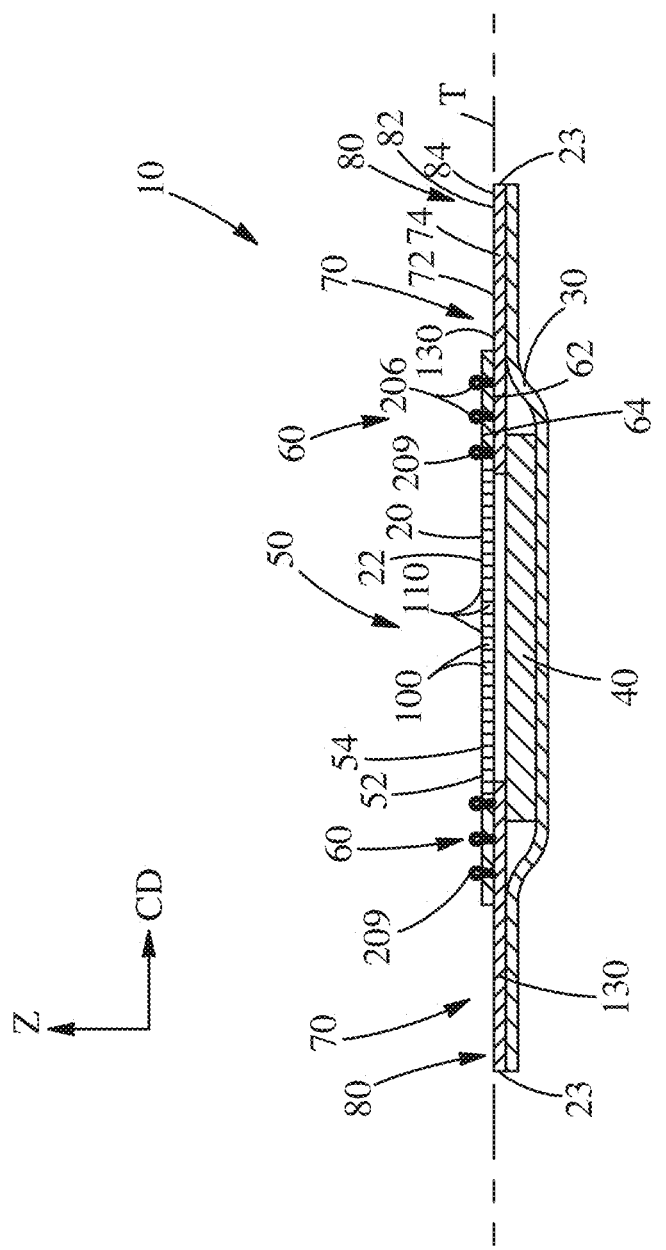
FIG. 7 is a schematic of a cross section of sanitary napkin, the cross section taken orthogonal to the longitudinal centerline.

In a similar embodiment, the central region 50 can comprise a film 100 having apertures 110 and the intermediate edge region 60 can comprises a film 100 in facing relationship, with a nonwoven 130. In such an arrangement, the film 100 in the central region 50 and the film 100 in the intermediate edge region 60 can be comprised of a single web of material, as illustrated in FIG. 7. The tufted fibers 206 in the intermediate edge region 60 can provide resistance to lateral fluid flow on the body facing surface of the topsheet 20 and/or provide for a soft texture to the portion of the topsheet 20 that might come into contact with the wearer's body adjacent to the opening between the labia. Also, as illustrated in FIG. 7, the body facing surface of topsheet 20 can be symmetric about the longitudinal centerline L with opposing intermediate edge regions 60 and edge regions 70.

Figure 8:
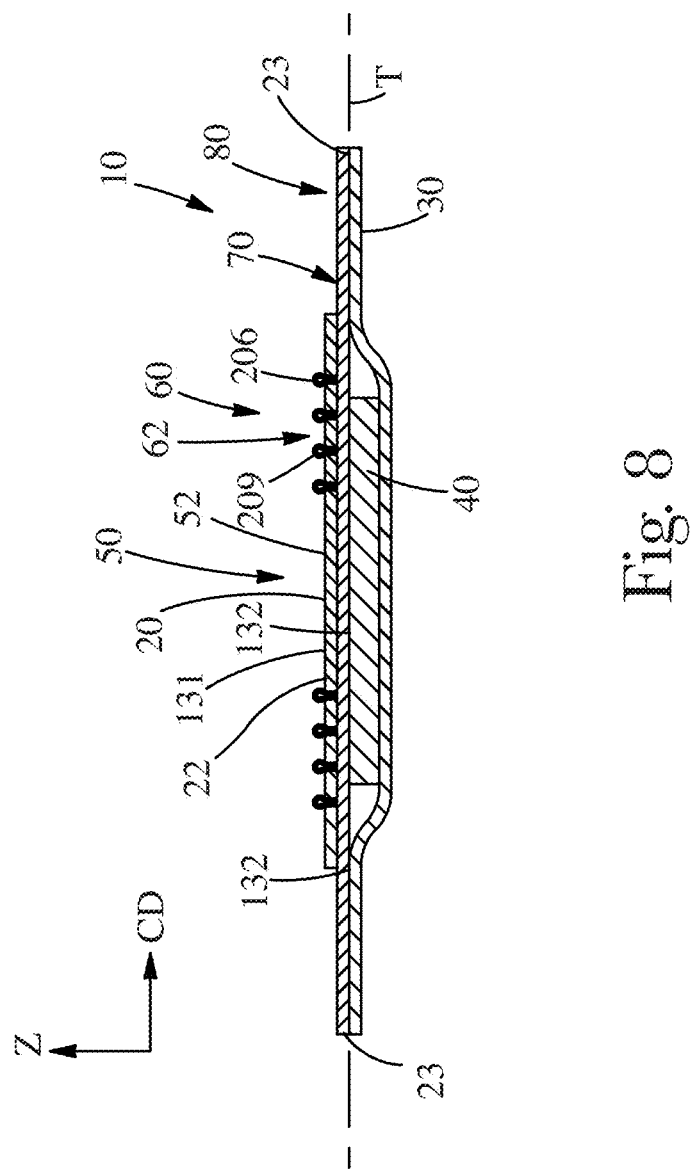
FIG. 8 is a schematic of a cross section of sanitary napkin, the cross section taken orthogonal to the longitudinal centerline.

As illustrated in FIG. 8, the central region 50 and the intermediate edge region 60 can comprise a first nonwoven 131 and a second nonwoven 132 in a facing relationship. An example of such an arrangement, in which the central region 50, intermediate edge region 60, and edge region 70 are disposed on a line generally parallel with the transverse centerline T, is shown in FIG. 8. As illustrated in FIG. 8, the first nonwoven 131 can form the central region body facing surface 52. The first nonwoven 131 can be designed such that the material is able to rapidly acquire fluid and the ability to resist rewet of the body facing surface of the topsheet 20. The first nonwoven 131 can comprise apertures 110 to provide for rapid acquisition of fluid. In the intermediate edge region 60, tufted fibers 206 from the second nonwoven 132 can protrude through the first nonwoven 131 to form tufts 209. In some embodiments, such an arrangement of tufted fibers 206 can act as a mechanical bond between the first nonwoven 131 and second nonwoven 132. The first nonwoven 131 and second nonwoven 132 can be arranged such that in the central region 50, the first nonwoven 131 is the central region body facing surface 52 and the second nonwoven 132 is between the first nonwoven 131 and the absorbent core 40.

Figure 9:
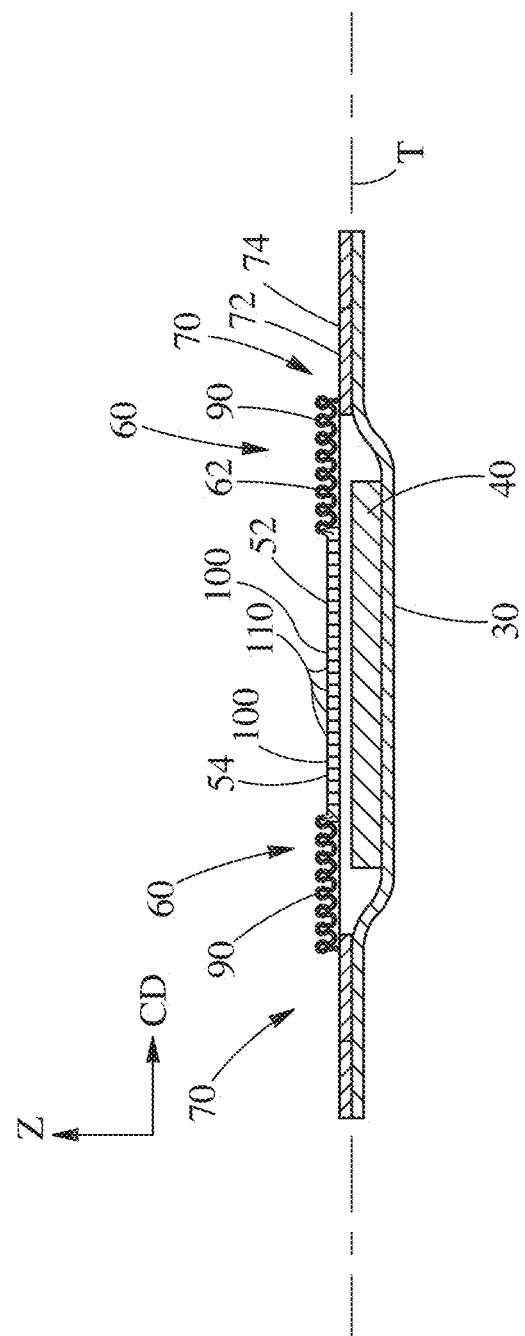
FIG. 9 is a schematic of a cross section of sanitary napkin, the cross section taken orthogonal to the longitudinal centerline.

The intermediate edge region texture 64 can be a film 100 having raised portions 90. An example of a design in which the intermediate edge region texture 64 is a film 100 having raised portions 90 that might be practical is one in which the central region texture 64 is a film 100 having apertures 110, as shown in FIG. 9. The film 100 in central region 50 and the intermediate edge region 60 can be comprised of a single unitary web of material. Without being bound by theory, raised portions 90 are thought to be able to provide for separation between the topsheet 20 and the wearer's body, which can provide for comfort during wear and improved skin health, and can be structured such that the raised portions 90 provide for a film that has a soft/cushiony feeling.

Figure 10:
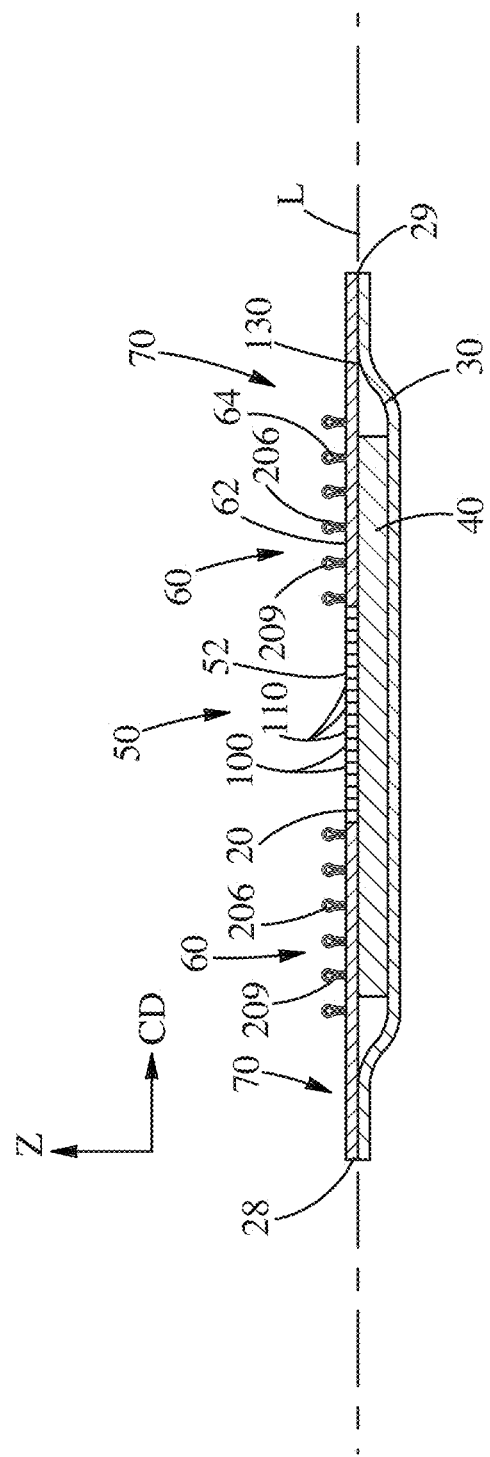
FIG. 10 is a schematic of a cross section of sanitary napkin, the cross section taken orthogonal to the longitudinal centerline.

The central region can comprise a film 100 comprising apertures 110 and the intermediate edge region 60 can comprise tufted fibers 206, as illustrated in FIG. 10. As illustrated in FIG. 10, the central region 50, intermediate edge region 60, and edge region 70 can be disposed on a line generally parallel with the transverse centerline T. Without being bound by theory, the tufted fibers 206 are believed to provide for softness of the topsheet 20 in areas away from the central region 50 and can provide resistance, or a barrier, to resist runoff of fluid on the body facing surface of the topsheet 20 in a direction generally aligned with the transverse centerline T. Also, as illustrated in FIG. 10, the topsheet 20 can be symmetric about a line parallel to the transverse centerline T, with opposing intermediate edge regions 60 and edge regions 70 on opposite sides of the central region 50.

Figure 11:
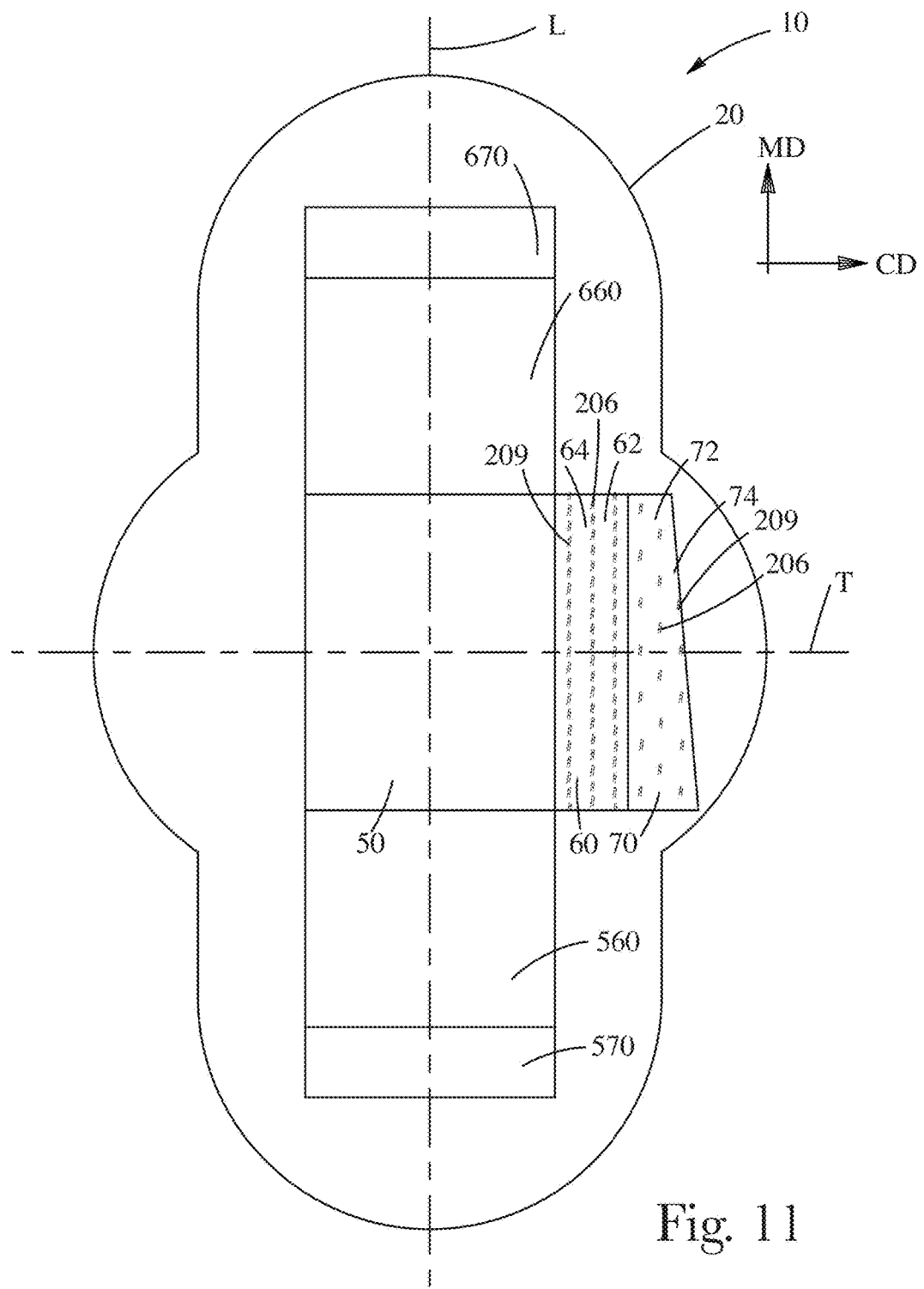
FIG. 11 is a schematic of a top view of a sanitary napkin.

The intermediate edge region 60 and the edge region 74 can comprise tufted fibers 206, which can form tufts 209, as shown in FIG. 11. The intermediate edge region 60 can have an intermediate edge region tuft area density and the edge region 70 can have an edge region tuft area density. A single tuft is comprised of a plurality of tufted fibers 206. The tuft area density is the number of tufts per unit area, area being measured in a plane parallel to the longitudinal centerline L and transverse centerline T. The intermediate edge region tuft area density can differ from the edge region tuft area density. For example, the intermediate region tuft area density can be greater than or less than the edge region tuft area density. Without being bound by theory, it is thought that by varying the tuft area density of different regions of the topsheet 20, the softness of the intermediate edge region texture 64 can be made to differ from the softness of edge region texture 74. Furthermore, the higher the tuft area density, the better the tufts are believed to provide for resistance to lateral flow on the topsheet.

Figure 12:
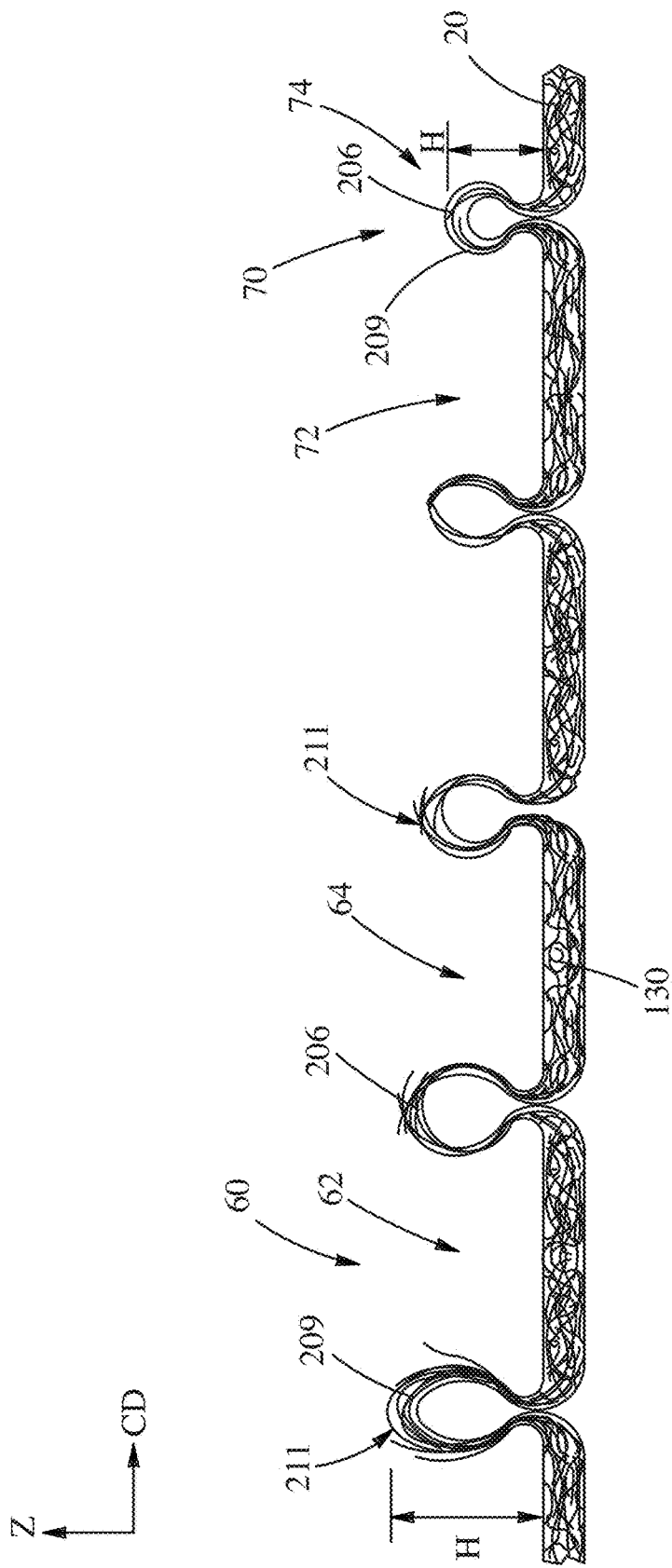
FIG. 12 is a schematic of a cross section of a nonwoven web having tufts.

The intermediate edge region 60 and the edge region 70 can comprise tufted fibers 206 and the intermediate edge region 60 can have an intermediate edge region tuft height H and the edge region 70 can have an edge region tuft height H, as shown in FIG. 12. The tuft height H is measured as the magnitude by which the tufted fibers 206 extend from the surface of the base material on the side from which the tufts protrude there from. The intermediate edge region tuft height H can differ from the edge region tuft height H. The intermediate edge region tuft height H can be greater than or less than the edge region tuft height. Without being bound by theory, it is thought that different tuft heights can provide for the desired degree of softness of a region, to provide for a barrier having sufficient resistance to lateral flow on the topsheet, and to provide separation of the absorbent article from the body where desired.

Figure 4:
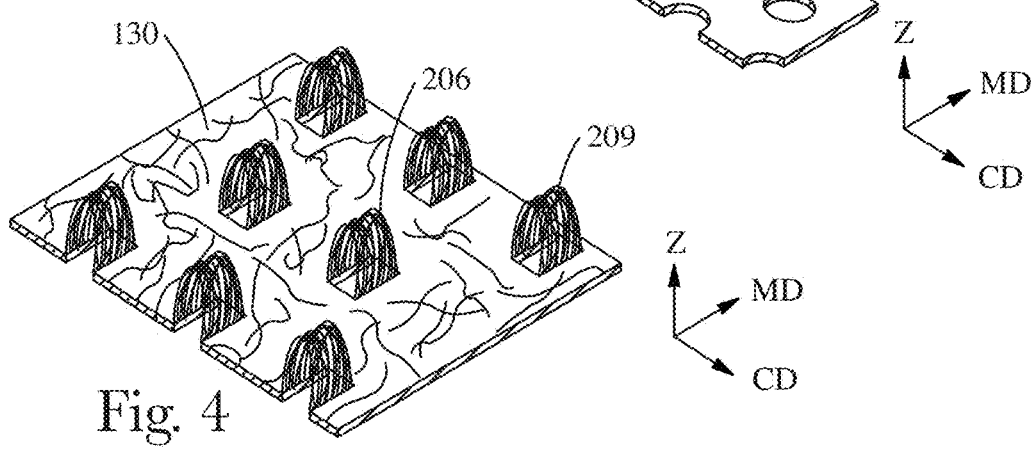
FIG. 4 is schematic of a nonwoven having tufts.

As shown in FIGS. 4 and 12, tufts 209 can comprise a plurality of tufted fibers 206 arranged in loops 211. A tuft will comprise more than one loop 211. A group of loops 211 may or may not be aligned to form the tuft. If the loops 211 are not aligned, there will be loops 211 in a variety of orientations. If the loops 211 are generally aligned, the tuft may appear as a tunnel shape, like that shown in FIG. 4. The loops 211 can extend generally perpendicular from the MD-CD plane of the web. Depending upon the number of loops 211 and how close the loops 211 are together, one loop 211 may hold up another loop 211 or the loops 211 may be touching. The loops 211 may extend out of the web on an angle.

A variety of textures can be provided to substrates for use in a topsheet 20. Materials believed to be practical include, but are not limited to, apertured film 100, apertured film 100 having raised portions 90, an apertured nonwoven, a nonwoven having tufts 209, and combinations thereof.

Figure 13:
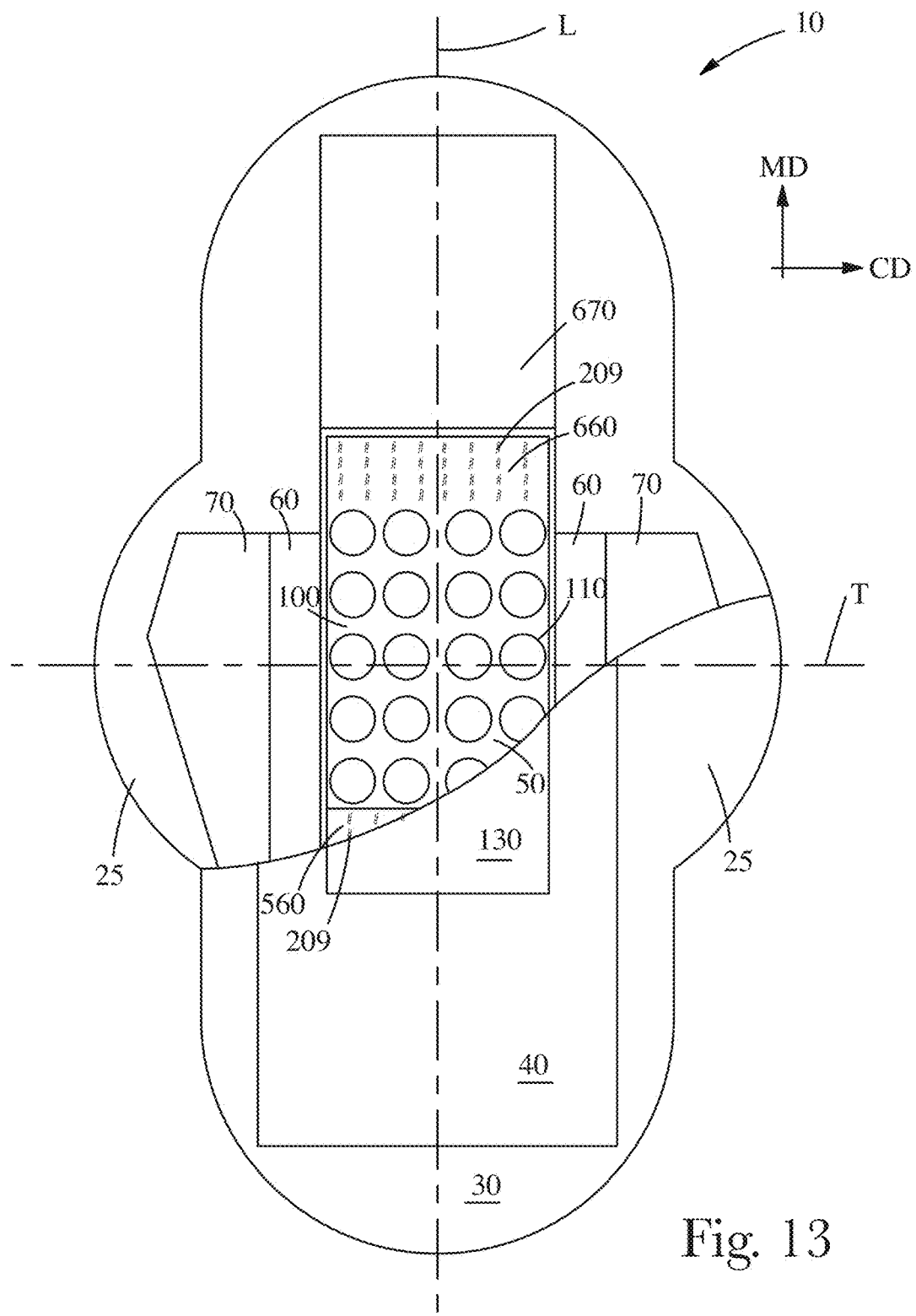
FIG. 13 is a schematic of a top view of a sanitary napkin.

The central region 50, the first end intermediate edge region 660, and the second end intermediate region 560 can comprise a film 100 in facing relationship with a nonwoven 130. An example of such an arrangement is illustrated in FIG. 13. The film 100 in the central region 50 can comprise apertures 110 to provide a pathway for fluid transport through the film 100. In the first end intermediate edge region 660 and the second intermediate region 560, tufted fibers 206 (forming tufts 209) from the nonwoven 130 can protrude through the film 100. The film 100 and nonwoven 130 can be arranged such that in the central region 50, the film 100 is the central region body facing surface 52 and the nonwoven 130 is between the film 100 and the absorbent core 40.

Figure 14:
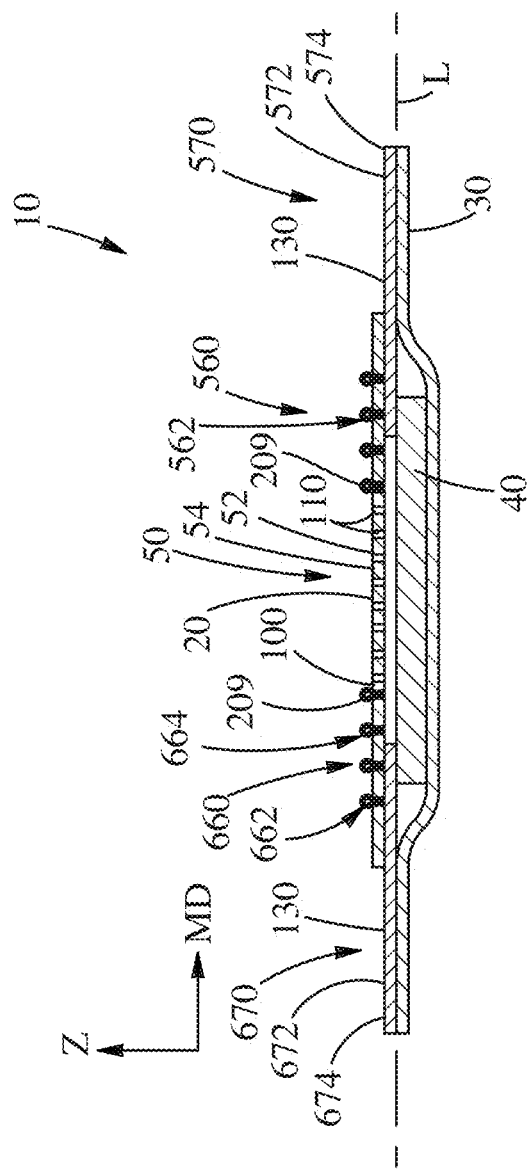
FIG. 14 is a schematic of a cross section of a sanitary napkin, the cross section taken orthogonal to the transverse centerline.

In a similar embodiment, the central region 50 can comprise a film 100 having apertures 110 and the first end intermediate edge region 660 and second end intermediate region 560 can comprises a film 100 in facing relationship, with a nonwoven 130. In such an arrangement, the film 100 in the central region 50 and the film 100 in the first end intermediate edge region 660 and second end intermediate region 560 can be comprised of a single web of material, as illustrated in FIG. 14. The tufted fibers 206 in the first end intermediate edge region 660 and second end intermediate region 560 can provide resistance to longitudinal fluid flow on the body facing surface of the topsheet 20 and/or provide for a soft texture to the portion of the topsheet 20 that might come into contact with the wearer's body adjacent to the opening between the labia. Also, as illustrated in FIG. 14, the body facing surface of topsheet 20 can be generally symmetric about the transverse centerline T.

Figure 15:
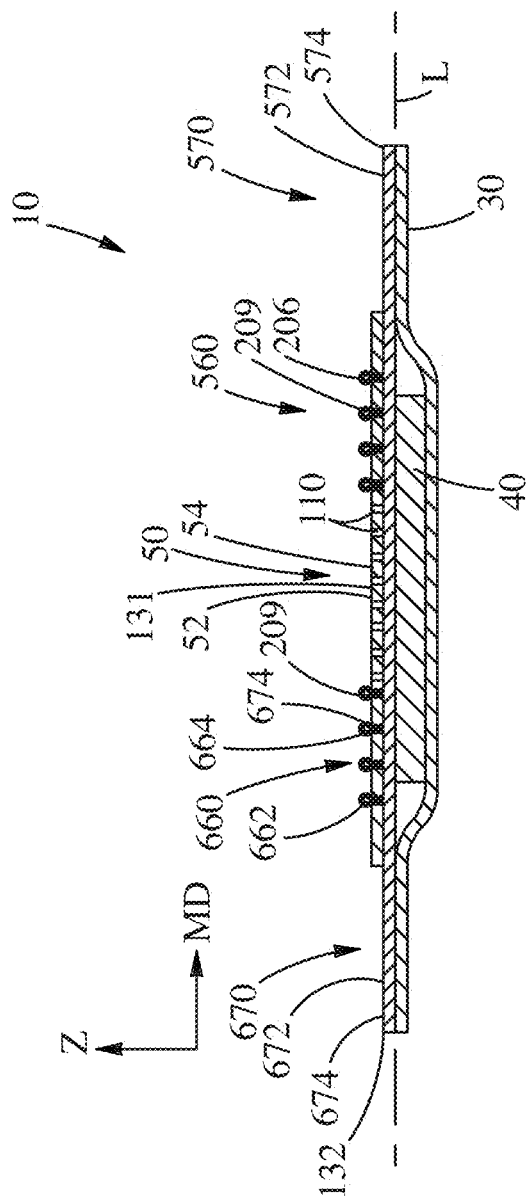
FIG. 15 is a schematic of a cross section of a sanitary napkin, the cross section taken orthogonal to the transverse centerline.

As illustrated in FIG. 15, the central region 50, first end intermediate edge region 660, and second end intermediate region 560 can comprise a first nonwoven 131 and a second nonwoven 132 in a facing relationship. An example of such an arrangement, in which the central region 50, first end intermediate region 660, and second end intermediate region 560 are disposed on a line generally parallel with the longitudinal centerline L, is shown in FIG. 15. As illustrated in FIG. 15, the first nonwoven 131 can form the central region body facing surface 52. The first nonwoven 131 can be designed such that the material is able to rapidly acquire fluid and the ability to resist rewet of the body facing surface of the topsheet 20. The first nonwoven 131 can comprise apertures 110 to provide for rapid acquisition of fluid. In the first end intermediate region 660, tufted fibers 206 from the second nonwoven 132 can protrude through the first nonwoven 131 to form tufts 209. In some embodiments, such an arrangement of tufted fibers 206 can act as a mechanical bond between the first nonwoven 131 and second nonwoven 132. The first nonwoven 131 and second nonwoven 132 can be arranged such that in the central region 50, the first nonwoven 131 is the central region body facing surface 52 and the second nonwoven 132 is between the first nonwoven 131 and the absorbent core 40. The second nonwoven 132 can be relatively hydrophilic compared to the first nonwoven 131.

The first end region 670 and the second end region 570 can comprise tufts 209. Without being bound by theory, a texture of tuft 209 near the front and rear portions of the absorbent article 10 can provide for protection for fluid running of the front and rear portions of the absorbent article 10.

Figure 16:
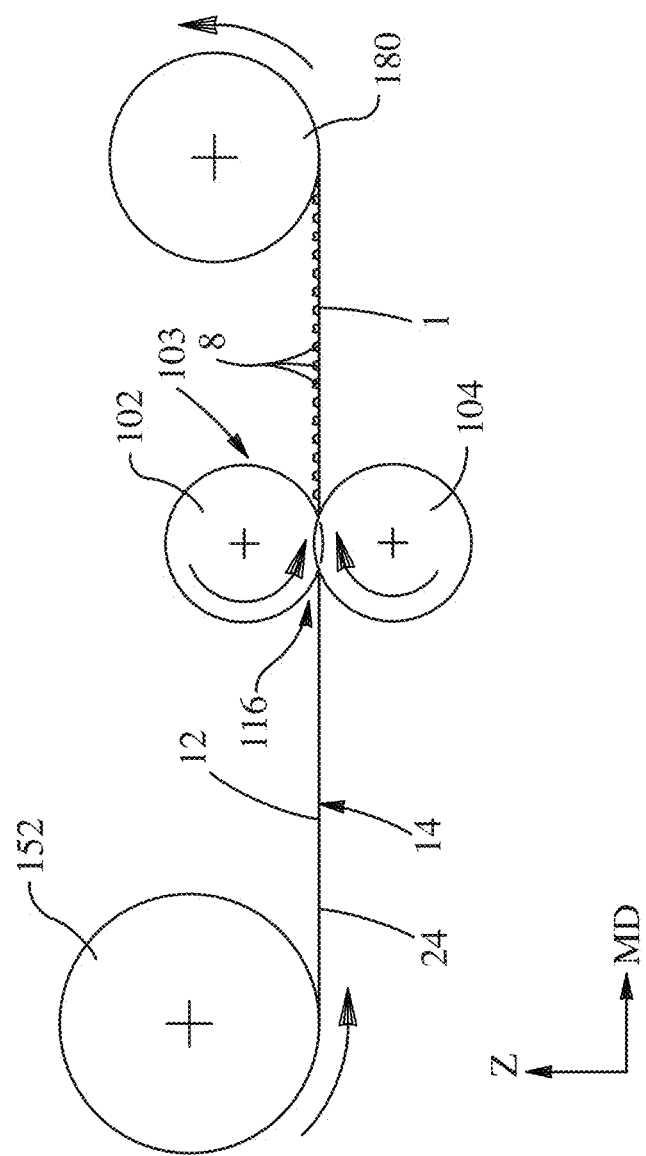
FIG. 16 is a schematic of an apparatus for forming apertures.

Apertures in a web 1 can be formed as illustrated in FIG. 16 to form apertures 110 in topsheet 20. The web 1 can be a film or a nonwoven. As shown in FIG. 16, web 1 can be formed from a generally planar, two dimensional precursor web 24 having a first side 12 and a second side 14. Precursor web 24 can be, for example, a polymer film, a nonwoven web, a woven fabric, a paper web, a tissue paper web, or a knitted fabric, or a multilayer laminate of any of the aforementioned. In general, the term "side" is used herein in the common usage of the term to describe the two major surfaces of generally two-dimensional webs, such as paper and films. In a composite or laminate structure, the first side 12 of the web 1 is the first side of one of the outermost layers or plies opposing one another, and the second side 14 is the second side of the other outermost layer or ply.

Precursor web 24 can be a polymeric film web. Polymeric film webs can be deformable. Deformable, as used herein, describes a material which, when stretched beyond its elastic limit, will substantially retain its newly formed conformation.

Polymeric film webs can include materials normally extruded or cast as films such as polyolefins, nylons, polyesters, and the like. Such films can be thermoplastic materials such as polyethylene, low density polyethylene, linear low density polyethylene, polypropylenes and copolymers and blends containing substantial fractions of these materials Precursor web 24 can be a nonwoven web. For nonwoven precursor webs 24, the precursor web 24 can comprise unbonded fibers, entangled fibers, tow fibers, or the like. Fibers can be extensible and/or elastic, and may be prestretched for processing. Fibers of precursor web 24 can be continuous, such as those produced by spunbonded methods, or cut to length, such as those typically utilized in a carded process. Fibers can be absorbent, and can include fibrous absorbent gelling materials. Fibers can be bicomponent, multiconstituent, shaped, crimped, or in any other formulation or configuration known in the art for nonwoven webs and fibers.

Nonwoven precursor webs 24 can be any known nonwoven webs including nonwoven webs 25 comprising polymer fibers having sufficient elongation properties to be formed into a nonwoven 130 having apertures 110. In general, the polymeric fibers can be bondable, either by chemical bond (e.g. by latex or adhesive bonding), pressure bonding, or thermal bonding. Nonwoven precursor web 24 can comprise about 100% by weight thermoplastic fibers. Nonwoven precursor web 24 can comprise as little as about 10% by weight thermoplastic fibers. Likewise, nonwoven precursor web 24 can comprise any amount by weight thermoplastic fibers in 1% increments between about 10% and about 100%.

The total basis weight of precursor web 24 (including laminate or multi-layer precursor webs 24) can range from about 8 gsm to about 500 gsm, depending on the ultimate use of the web 1, and can be produced in 1 gsm increments between about 8 and about 500 gsm. The constituent fibers of nonwoven precursor web 24 can be polymer fibers, and can be monocomponent, bicomponent and/or biconstituent fibers, hollow fibers, non-round fibers (e.g., shaped (e.g., trilobal) fibers or capillary channel fibers), and can have major cross-sectional dimensions (e.g., diameter for round fibers, long axis for elliptical shaped fibers, longest straight line dimension for irregular shapes) ranging from about 0.1 to about 500 microns in 0.1 micron increments.

Supply roll 152 rotates in the direction indicated by the arrow in FIG. 16 as precursor web 24 is moved in the machine direction by means known in the art, including over or around any of various idler rollers, tension-control rollers, and the like to the nip 116 of a pair of counter-rotating rolls 102 and 104. The rolls 102 and 104 can comprise forming apparatus 103. The pair of rolls 102 and 104 can operate to form volcano shaped structures 8 and apertures in precursor web 24. Apertured web 1 can be taken up on wind up roll 180.

There are a variety of approaches for creating apertures 110 in webs. Factors that can influence the approach selected for creating apertures include, but are not limited to, whether the precursor web 24 is a nonwoven or polymeric film, the desired geometry of the aperture, the desired processing speed, and the amount of control of the process that is desired.

Figure 17:
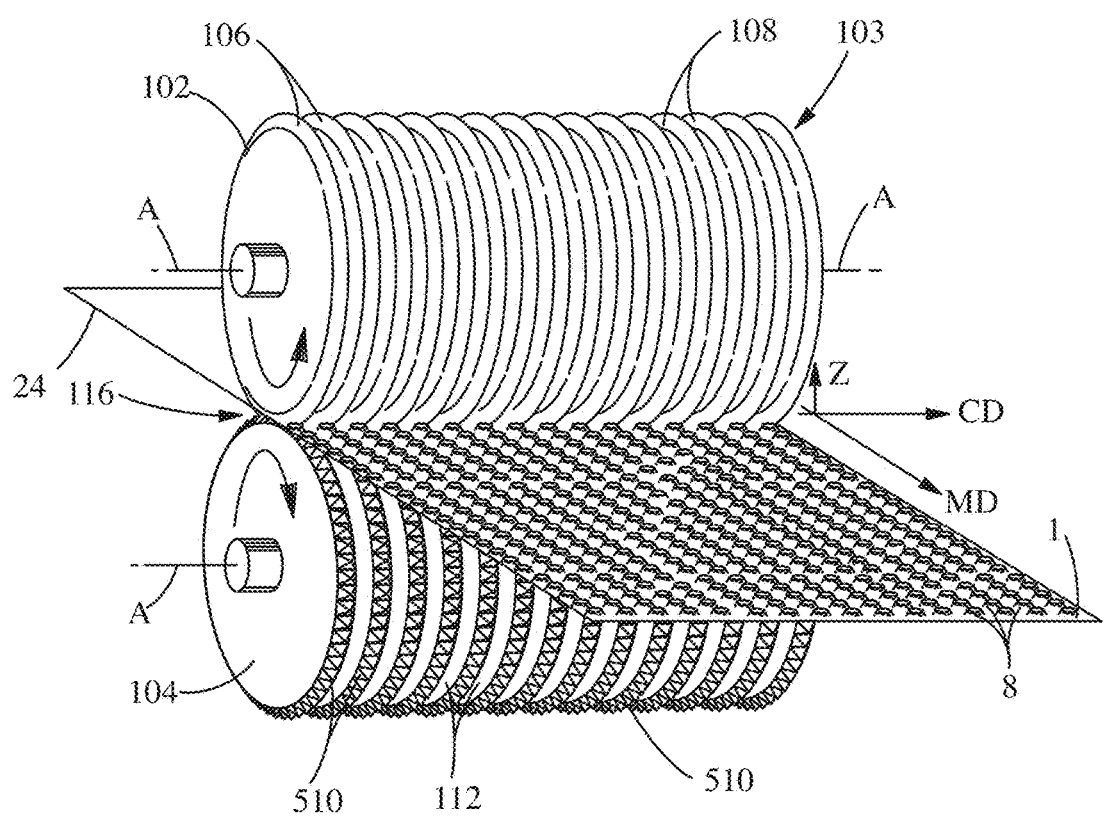
FIG. 17 is a schematic of an apparatus for forming apertures.

An approach for forming apertures in polymeric film webs and nonwoven webs is to employ a pair of intermeshing rolls 102 and 104, as shown in FIG. 17 and disclosed in U.S. patent application Ser. No. 11/249,618 by O'Donnell et al. Referring to FIG. 17, there is shown in more detail the portion of the apparatus shown in FIG. 16 that can form apertured web 1. Forming apparatus 103 can comprise a pair of steel intermeshing rolls 102 and 104, each rotating about an axis A, the axes A being parallel and in the same plane. Forming apparatus 103 can be designed such that precursor web 24 remains on roll 104 through a certain angle of rotation. FIG. 17 shows in principle what happens as precursor web 24 goes straight through nip 116 on forming apparatus 103 and exits as apertured web 1. Precursor web 24 or apertured web 1 can be partially wrapped on either of rolls 102 or 104 through a predetermined angle of rotation prior to (for precursor web 24) or after (for web 1) nip 116.

Roll 102 can comprise a plurality of ridges 106 and corresponding valleys 108 which can extend unbroken about the entire circumference of roll 102. Depending on what kind of pattern is desired in apertured web 1, roll 102 can comprise ridges 106 wherein portions have been removed, such as by etching, milling or other machining processes, such that some or all of ridges 106 are not circumferentially continuous, but have breaks or gaps. Ridges 106 can be spaced apart from one another along the axis A of roll 102. For instance, the middle third of roll 102 can be smooth and the outer thirds of roll 102 can have a plurality of ridges that are spaced apart from one another. Similarly, ridges 106 on the middle third of roll 102 can be spaced more closely together than ridges 106 on the outer thirds of roll 102. The breaks or gaps, in either the circumferential direction, axial direction, or both directions, can be arranged to form a pattern, including geometric patterns such as circles or diamonds. In one embodiment, roll 102 can have teeth, similar to the teeth 510 on roll 104, described below. In this manner, it is possible to have three dimensional apertures having portions extending outwardly on both sides of apertured web 1.

Roll 104 can comprise a plurality of rows of circumferentially-extending ridges that have been modified to be rows of circumferentially-spaced teeth 510 that extend in spaced relationship about at least a portion of roll 104. The individual rows of teeth 510 of roll 104 can be separated by corresponding grooves 112. In operation, rolls 102 and 104 intermesh such that the ridges 106 of roll 102 extend into the grooves 112 of roll 104 and the teeth 510 of roll 104 extend into the valleys 108 of roll 102. Both or either of rolls 102 and 104 can be heated by means known in the art such as by incorporating hot oil filled rollers or electrically-heated rollers. Alternatively, both or either of the rolls may be heated by surface convection or by surface radiation.

Figure 18:
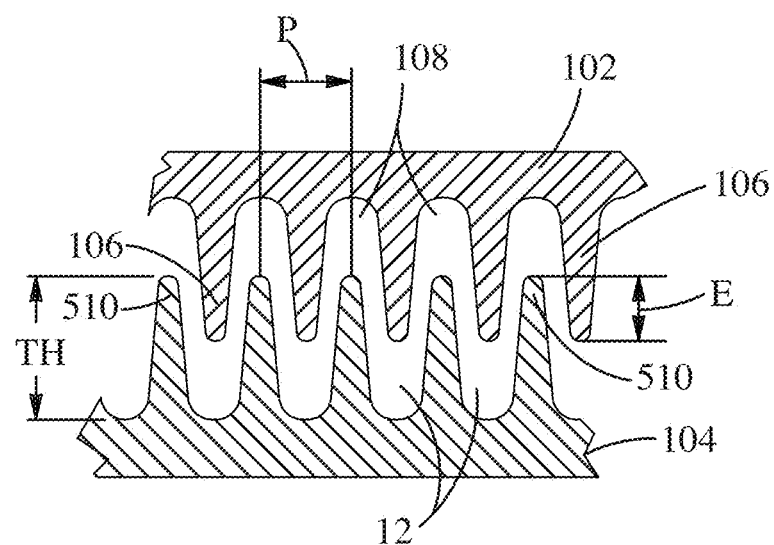
FIG. 18 is a schematic of intermeshing rolls.

A schematic of a cross section of a portion of the intermeshing rolls 102 and 104 including ridges 106 and representative teeth 510 is shown in FIG. 18. As shown, teeth 510 have a tooth height TH (note that TH can also be applied to ridge 106 height and tooth height and ridge height can be equal) and a tooth-to-tooth spacing (or ridge-to-ridge spacing) referred to as the pitch P. As shown, depth of engagement, (DOE) E is a measure of the level of intermeshing of rolls 102 and 104 and is measured from tip of ridge 106 to tip of tooth 510. The depth of engagement E, tooth height TH, and pitch P can be varied as desired depending on the properties of precursor web 24 and the desired characteristics of apertured web 1. The rolls 102 and 104 can be made of wear resistant stainless steel.

The aperture area density (the number of apertures 110 per unit area) can be varied from about 1 aperture/cm$^2$ to about 6 apertures/cm$^2$ to about 60 apertures/cm$^2$, in increments of 1 aperture/cm$^2$. There can be, for example, at least about 10 apertures/cm$^2$, or at least about 25 apertures/cm$^2$.

As can be understood with respect to forming apparatus 103, apertures can be made by mechanically deforming precursor web 24 that can be described as generally planar and two dimensional. By "planar" and "two dimensional" is meant simply that the precursor web 24 may be flat relative to a finished apertured web 1 having a distinct, out-of-plane, z-direction three-dimensionality imparted due to the formation of truncated generally conical shaped structures 8. "Planar" and "two-dimensional" are not meant to imply any particular flatness, smoothness or dimensionality and a soft, fibrous non-woven web can be planar in its as-made condition.

As precursor web 24 goes through the nip 116, the teeth 510 of roll 104 enter valleys 108 of roll 102 and simultaneously urge material out of the plane of precursor web 24 to form apertures 110, the apertures being defined by the rim of the truncated generally conical shaped structures 8. In effect, teeth 510 "push" through precursor web 24. As the tip of teeth 510 push through precursor web 24 the web material can be urged by the teeth 510 out of the plane of precursor web 24 and can be stretched and/or plastically deformed in the z-direction, creating out-of-plane geometry characterized by conical shaped structures 8 and apertures 110. The truncated generally conical shaped structures 8 can be thought of as volcano-shaped structures.

Figure 19:
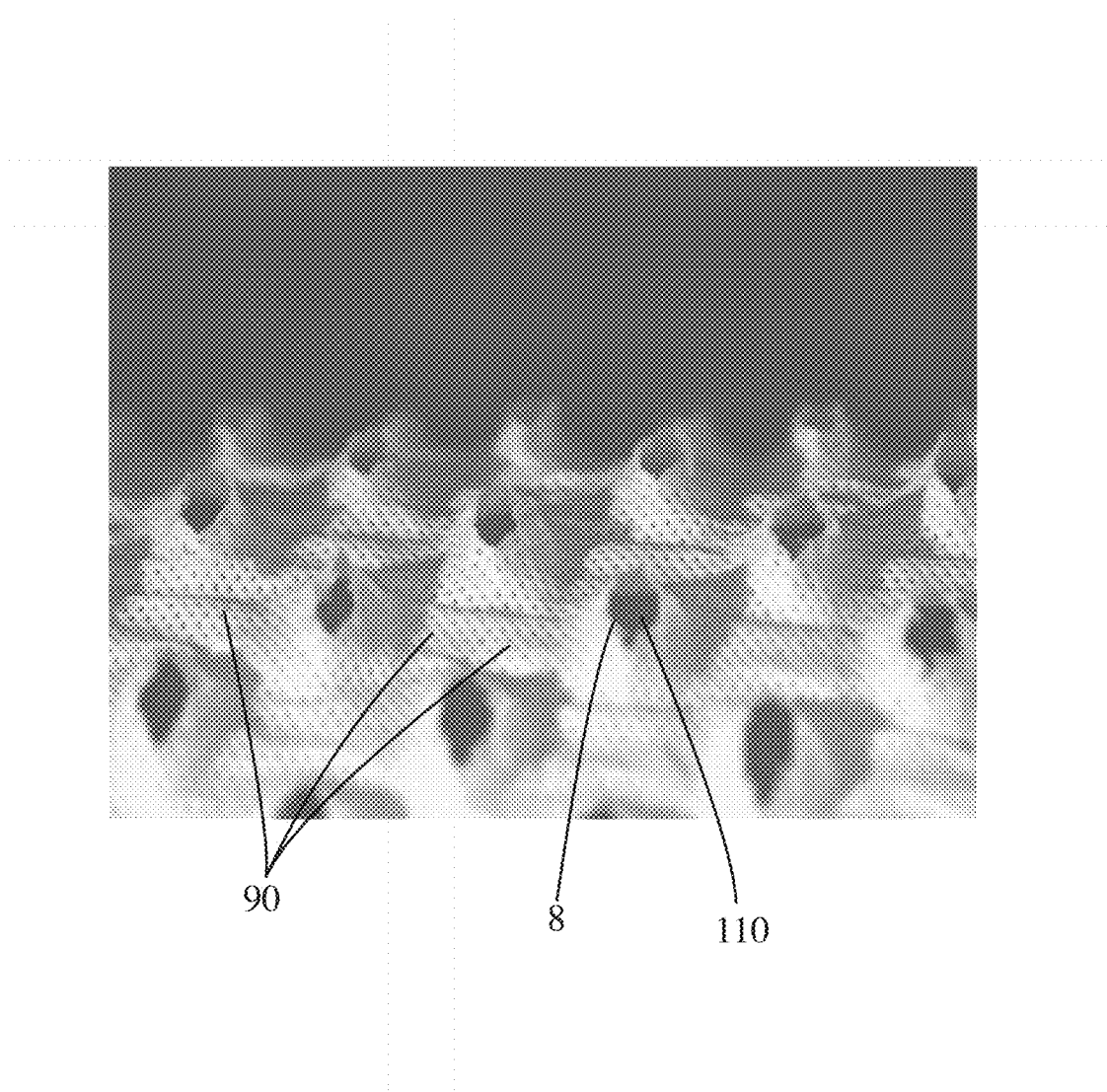
FIG. 19 is an apertured web.

FIG. 19 shows an embodiment of a three-dimensional apertured web 1 in which the precursor web 24 was not a flat film but rather was a film that was pre-textured with microscopic raised portions 90 that can be formed for use in topsheet 20. Raised portions 90 can be bumps, holes, or the like. In the embodiment shown, raised portions 90 are also volcano-shaped micro-apertures, formed by a hydroforming process. A suitable hydroforming process is the first phase of the multiphase hydroforming process disclosed in U.S. Pat. No. 4,609,518, issued to Curro et al. on Sep. 2, 1986. The hydroforming screen utilized for the web shown in FIG. 19 was a "100 mesh" screen and the film was obtained from Tredegar Film Products, Terre Haute, Ind. Apertures 110, defined by the rims of the truncated generally conical shaped structures 8, can be formed by teeth 510 of roll 104 in forming apparatus 103. The truncated generally conical shaped structures 8 can be oriented in a topsheet 20 such that the rims of the truncated generally conical shaped structures 8 are on the body facing side of the topsheet. The truncated generally conical shaped structures 8 can be oriented in a topsheet 20 such that the rims of the truncated generally conical shaped structures are on the garment facing side of the topsheet 20. The truncated generally conical shaped structures 8 can be oriented in a topsheet 20 such that some of the rims of the truncated generally conical shaped structures are on the garment facing side of the topsheet 20 and some of the rims of the truncated generally conical shaped structures 8 are on the body facing side of the topsheet 20.

The apertures of the film embodiments shown in FIG. 19 were made on an apparatus like that shown in FIG. 17, where the forming apparatus 103 is arranged to have one patterned roll, e.g., roll 104, and one non-patterned roll 102. In certain embodiments nip 116 can be formed by using two patterned rolls having either the same or differing patterns, in the same or different corresponding regions of the respective rolls. Such an apparatus can produce webs with apertures protruding from both sides of the apertured web 1, as well as macro-texture, e.g., aberrations, micro-apertures, or micro-patterns, in the web 1. Likewise, it may be desirable to have multiple forming apparatuses 103 such that apertured web 1 is re-processed to have additional truncated generally conical shaped structures 8 and/or apertures. For example, a greater aperture area density of truncated generally conical shaped structures 8 on apertured web 1 can be achieved by processing precursor web 24 through two or more forming apparatuses 103 or by decreasing the spacing between teeth 510.

The number, aperture area density, size, geometry, and out of plane geometry associated with the apertures can be varied by changing the number, spacing between, geometry, and size of teeth 510 and making corresponding dimensional changes as necessary to roll 104 and/or roll 102.

Figure 20:
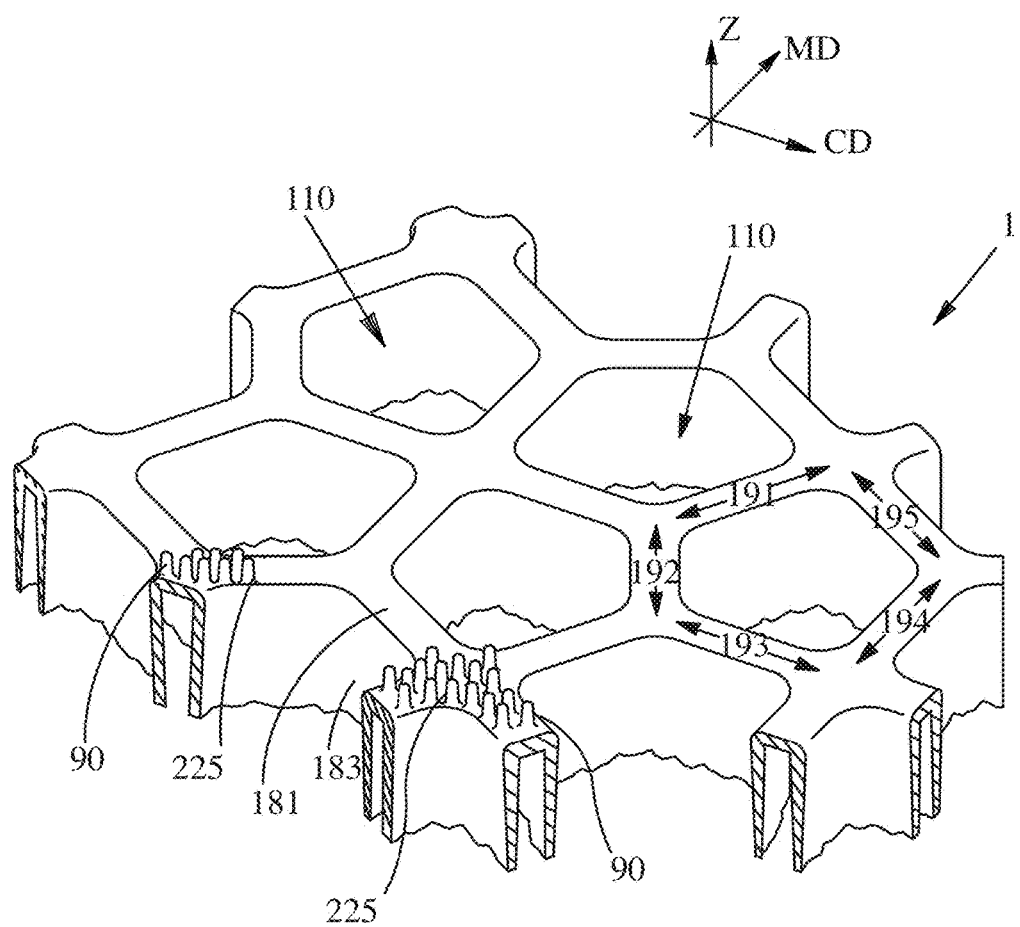
FIG. 20 is a schematic of a film having raised portions.

Raised portions 90 can be fibrils to provide texture that provides for a tactile impression of softness, as illustrated in FIG. 20. FIG. 20 is an enlarged, partially segmented perspective illustration of a fluid pervious, macroscopically-expanded, three-dimensional apertured web 1. Apertured web 1 can have apertures 110 that provide for fluid communication between opposing sides of the apertured web 1. The apertures 110 can be defined by a continuous network of interconnecting members, e.g., members 191, 192, 193, 194, and 195 interconnected to one another. The shape of apertures 110 may be polygons including, but not limited to, squares, hexagons, etc., in an ordered or random pattern. Apertures 110 can be in the shape of modified ovals, and in one embodiment apertures 110 can be in the general shape of a tear drop. Polymer web 1 exhibits a plurality of raised portions 90 in the form of hair-like fibrils 225, described more fully below.

In a three-dimensional, microapertured polymeric web 1, each interconnecting member can comprises a base portion, e.g., base portion 181 and each base portion can have a sidewall portions, e.g., sidewall portions 183 extending from each longitudinal edge thereof. Sidewall portions 183 can extend generally in the direction of the opposing surface of the web 1 and join to sidewalls of adjoining interconnecting members.

Figure 21:
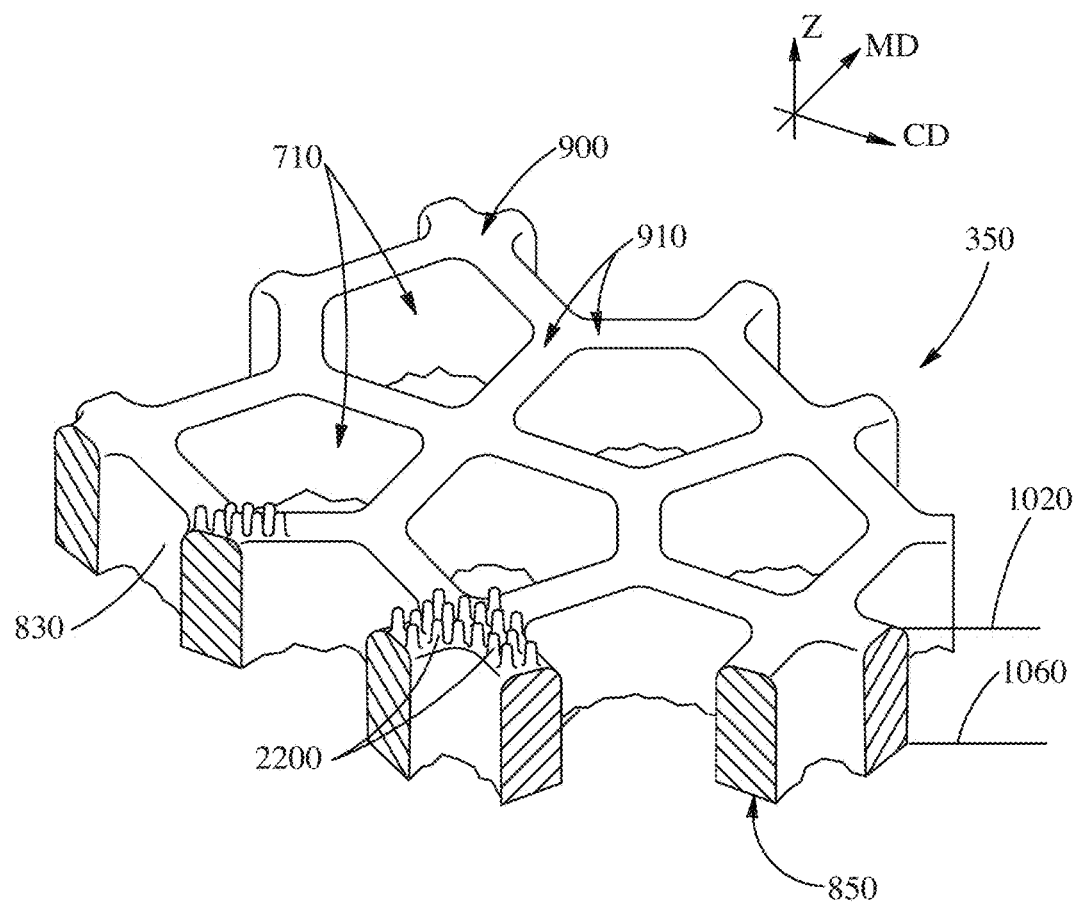
FIG. 21 is a schematic of a forming screen.

Raised portions 90 can be formed in a web using a forming structure 350 such as, for example, that shown in FIG. 21. FIG. 21 shows a portion of a forming structure of the present invention 350 in partial perspective view. The forming structure 350 exhibits a plurality of forming structure apertures 710 defined by forming structure interconnecting members 910. Forming structure apertures 710 permit fluid communication between opposing surfaces, that is, between forming structure first surface 900 in the plane of the first surface 1020 and forming structure second surface 850 in the plane of the second surface 1060. Forming structure sidewall portions 830 extend generally between the forming structure first surface 900 and forming structure second surface 850. Protrusions 2200 can extend from forming structure first surface 900 and can be generally columnar, pillar-like forms.

A comparison of FIG. 21 with FIG. 20 shows the general correspondence of forming structure 350 with polymeric web 1. That is, the three-dimensional protrusions 2200 and forming structure apertures 710 of forming structure 350 can have a generally one-to-one correspondence to the raised portions 90 and apertures 110, respectively, of polymeric web 1.

Raised portions 90 can be formed in a polymeric web 1 by the forming structure 350 using a variety of processes known in the art, including, but not limited to, hydro-forming, vacuum forming, and direct cast. The forming structure 350 can be arranged as a cylindrical drum that rotates about the axial axis. U.S. Pat. No. 7,402,723 by Stone et al., issued Jul. 22, 2008 discloses polymeric webs having raised portions and methods for forming such polymeric webs. A polymeric web, such as that employed in Always Ultra sanitary napkins, marked by Procter & Gamble Co., Cincinnati, Ohio, can be practical for the topsheet 20 or components/portions thereof.

Raised portions 90 other than generally columnar hollow fibrils are contemplated. Softness can be beneficial when webs 1 are employed as part of a topsheet in a disposable absorbent article. A soft, compliant topsheet 20 for an absorbent article 10 can be achieved when the apertured web 1 is used with the second side 14 having raised portions 90 as the body-facing surface of the article. In some embodiments, raised portions 90 can be on the garment facing side of the topsheet 20 to possibly provide for a different level of comfort or different properties related to flow of fluids.

Figure 22:
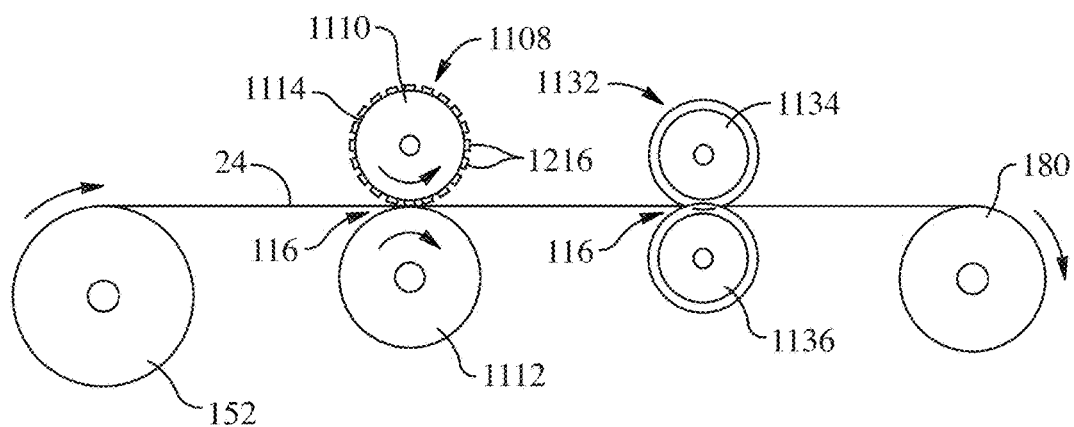
FIG. 22 is a schematic of an apparatus for forming apertures.

A technique for forming a nonwoven 130 having apertures 110 that can be used to form topsheet 20 is illustrated in FIG. 22. Referring to FIG. 22 there is schematically illustrated a process and apparatus for selectively aperturing a nonwoven web suitable for use as a topsheet 20 on an absorbent article 10. U.S. patent application Ser. No. 11/249,618, U.S. Pat. No. 5,714,107, and U.S. Pat. No. 5,628,097 disclose apertures, apparatuses, and methods for creating apertures 110 in nonwoven webs.

Nonwoven precursor web 24 can be unwound from a supply roll 152 and travel in a direction indicated by the arrows associated therewith as the supply roll 152 rotates in the direction indicated by the arrows associated therewith. The nonwoven precursor web 24 passes through a nip 116 of the web weakening roller arrangement 1108 formed by calender roll 1110 and smooth anvil roller 1112.

The nonwoven precursor web 24 may be formed by known nonwoven extrusion processes, such as, for example, known meltblowing processes or known spunbonding processes, and passed directly through the nip 116 without first being bonded and/or stored on a supply roll.

The nonwoven precursor web 24 may be extensible, elastic, or nonelastic. The nonwoven precursor web 24 may be a spunbonded web, a meltblown web, or a bonded carded web. If the nonwoven precursor web 24 is a web of meltblown fibers, it may include meltblown microfibers. The nonwoven precursor web 24 may be made of fiber forming polymers such as, for example, polyolefins. Polyolefins include one or more of polypropylene, polyethylene, ethylene copolymers, propylene copolymers, and butene copolymers.

In another embodiment, the nonwoven precursor web 24 may be a multilayer material having, for example, at least one layer of a spunbonded web joined to at least one layer of a meltblown web, a bonded carded web, or other suitable material. For example, the nonwoven precursor web 24 may be a multilayer web having a first layer of spunbonded polypropylene having a basis weight from about 0.2 to about 8 ounces per square yard, a layer of meltblown polypropylene having a basis weight from about 0.2 to about 4 ounces per square yard, and a second layer of spunbonded polypropylene having a basis weight from about 0.2 to about 8 ounces per square yard. Alternatively, the nonwoven web may be a single layer of material, such as, for example, a spunbonded web having a basis weight from about 0.2 to about 10 ounces per square yard or a meltblown web having a basis weight from about 0.2 to about 8 ounces per square yard.

The nonwoven precursor web 24 may be joined to a polymeric film to form a laminate. Suitable polymeric film materials include but are not limited to polyolefins, such as polyethylenes, polypropylene, ethylene copolymers, propylene copolymers, and butene copolymers; nylon (polyamide); metallocene catalyst-based polymers; cellulose esters; poly (methyl methacrylate); polystyrene; poly(vinyl chloride); polyester; polyurethane; compatible polymers; compatible copolymers; and blends, laminates and/or combinations thereof.

The nonwoven precursor web 24 may also be a composite made up of a mixture of two or more different fibers or a mixture of fibers and particles. Such mixtures may be formed by adding fibers and/or particulates to the gas stream in which the meltblown fibers or spunbond fibers are carried so that an intimate entangled co-mingling of fibers and other materials, e.g., wood pulp, staple fibers, and particles, occurs prior to collection of the fibers.

The nonwoven precursor web 24 of fibers can be joined by bonding to form a coherent web structure. Suitable bonding techniques include, but are not limited to, chemical bonding, thermobonding, such as point calendering, hydroentangling, and needling.

One or both of the patterned calender roll 1110 and the smooth anvil roller 1112 may be heated and the pressure between the two rollers may be adjusted to provide the desired temperature, if any, and pressure to concurrently weaken and melt-stabilize the nonwoven precursor web 24 at a plurality of locations.

The patterned calender roll 1110 is configured to have a cylindrical surface 1114, and a plurality of protuberances 1216 which extend outwardly from cylindrical surface 1114. The protuberances 1216 are disposed in a predetermined pattern with each protuberance 1216 being configured and disposed to precipitate a weakened, melt-stabilized location in the nonwoven precursor web 24 to create a predetermined pattern of weakened, melt-stabilized locations in the nonwoven precursor web 24. Also shown in FIG. 22 and discussed further below are incremental stretching system 1132, and incremental stretching rollers 1134 and 1136.

Prior to entering nip 116, the coherent nonwoven web comprises a plurality of fibers joined together by point calendered bonds to form a coherent web structure.

Patterned calender roll 1110 can have a repeating pattern of protuberances 1216 which extend about the entire circumference of cylindrical surface 1114. Alternatively, the protuberances 1216 may extend around a portion, or portions of the circumference of cylindrical surface 1114.

Figure 23:
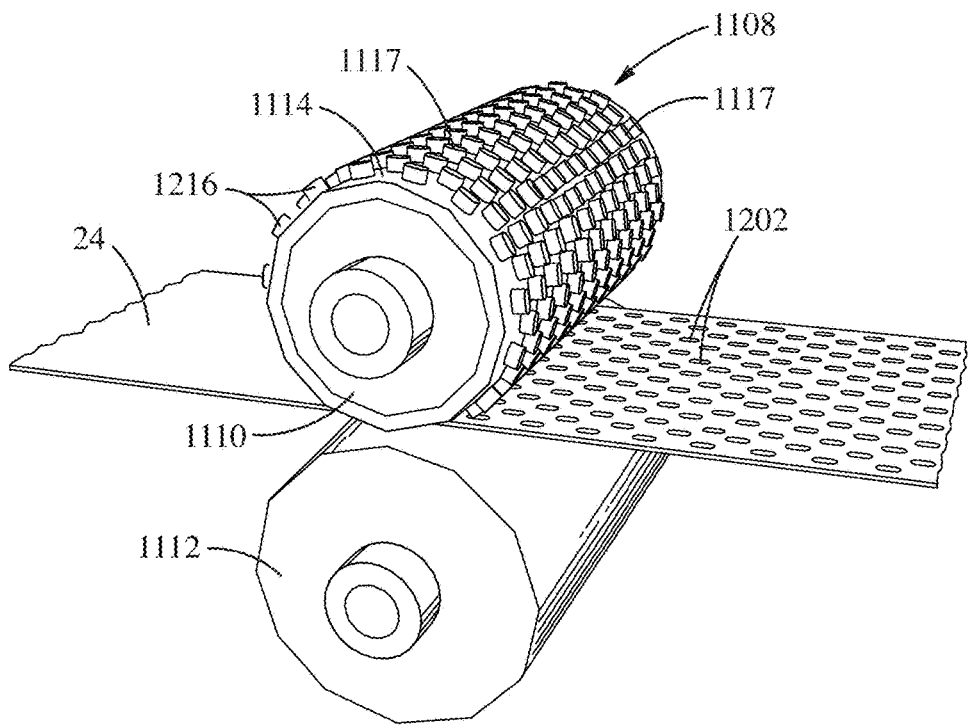
FIG. 23 is a schematic of an apparatus for forming apertures.

By way of example and not to be limiting, protuberances 1216 can be truncated conical shapes which extend radially outwardly from cylindrical surface 1114 and which have elliptical distal end surfaces 1117, as shown in FIG. 23. Other suitable shapes for distal end surfaces 1117 include, but are not limited to circular, square, rectangular, etc. The patterned calender roll 1110 can be finished so that all of the end surfaces 1117 lie in an imaginary right circular cylinder which is coaxial with respect to the axis of rotation of calender roll 1110.

Protuberances 1216 can be blades having their long axis oriented circumferentially about the patterned calender roll 1110. Protuberances 1216 can be blades having their long axis oriented parallel to the rotating axis of the calender roll 1110.

The protuberances may be disposed in any predetermined pattern about patterned calender roll 1110. After passing through the weakening roller arrangement 1108, the precursor web 24 can have a plurality of melt stabilized locations 1202. Anvil roller 1112, can be a smooth surfaced, right circular cylinder of steel.

From the weakening roller arrangement 1108, the nonwoven precursor web 24 passes through nip 116 formed by the incremental stretching system 1132 employing opposed pressure applicators having three-dimensional surfaces which at least to a degree are complementary to one another.

Figure 24:
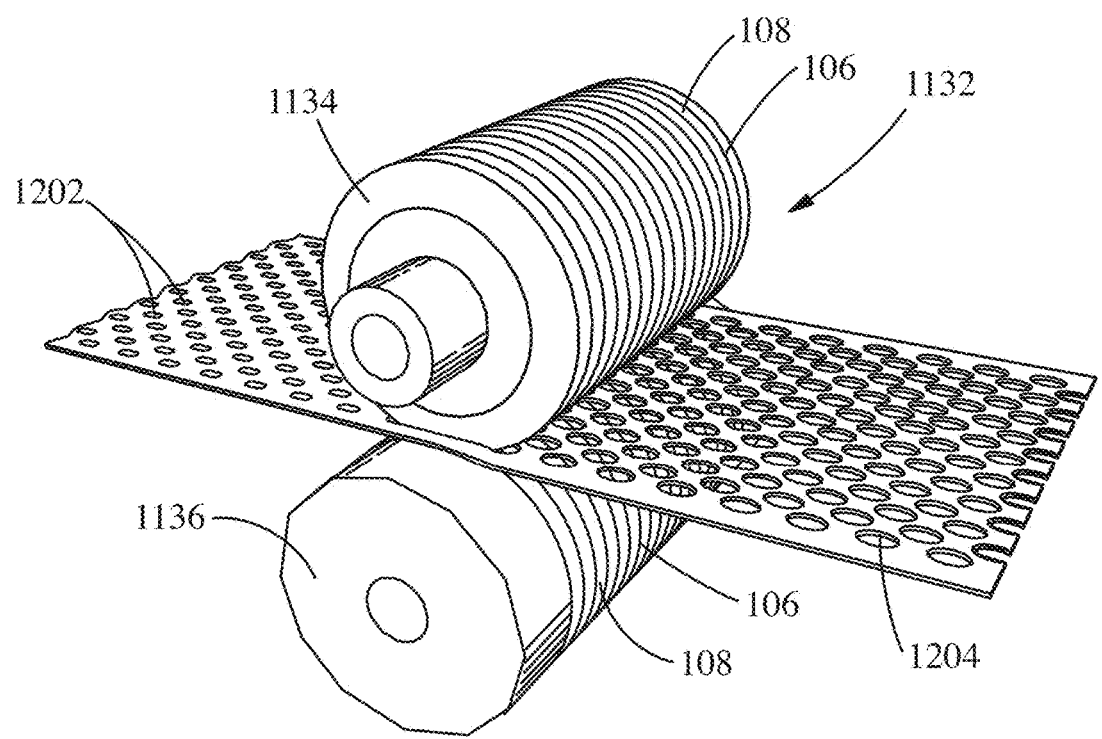
FIG. 24 is a schematic of an incremental stretching apparatus.

Referring now to FIG. 24, there is shown a fragmentary enlarged view of the incremental stretching system 1132 comprising incremental stretching rollers 1134 and 1136. The incremental stretching roller 1134 can comprise a plurality of ridges 106 and corresponding valleys 108 that extend about the entire circumference of incremental stretching roller 1134 or only partially about the circumference of incremental stretching roller 1134. Incremental stretching roller 1136 includes a plurality of complimentary ridges 106 and a plurality of corresponding valleys 108. The ridges 106 on incremental stretching roller 1134 intermesh with or engage the valleys 108 on incremental stretching roller 1136 and the ridges 106 on incremental stretching roller 1136 intermesh with or engage the valleys 108 on incremental stretching roller 1134. As the nonwoven precursor web 24 having weakened, melt-stabilized locations 1202 passes through the incremental stretching system 1132, the nonwoven precursor web 24 is subjected to tensioning in the CD or cross-machine direction causing the nonwoven precursor web 24 to be extended in the CD direction. Alternatively, or additionally, the nonwoven precursor web 24 may be tensioned in the MD or machine direction. The tensioning force placed on the nonwoven precursor web 24 can be adjusted such that it causes the weakened, melt-stabilized locations 1202 to rupture creating a plurality of formed SAN apertures 1204 (SAN standing for Stretch Apertured Nonwoven) coincident with the weakened melt-stabilized locations 1202 in the nonwoven precursor web 24 to form apertured web 1. However, the bonds of the nonwoven precursor web 24 can be strong enough such that they do not rupture during tensioning, thereby maintaining the nonwoven web in a coherent condition even as the weakened, melt-stabilized locations rupture.

Other structures of incremental stretching mechanisms suitable for incrementally stretching or tensioning the nonwoven web are described in International Patent Publication No. WO 95/03765, published Feb. 9, 1995, in the name of Chappell, et al.

The nonwoven apertured web 1 can be taken up on wind-up roll 180 and stored. Alternatively, the nonwoven apertured web 1 may be fed directly to a production line where it is used to form a topsheet on a disposable absorbent article.

Figure 25:
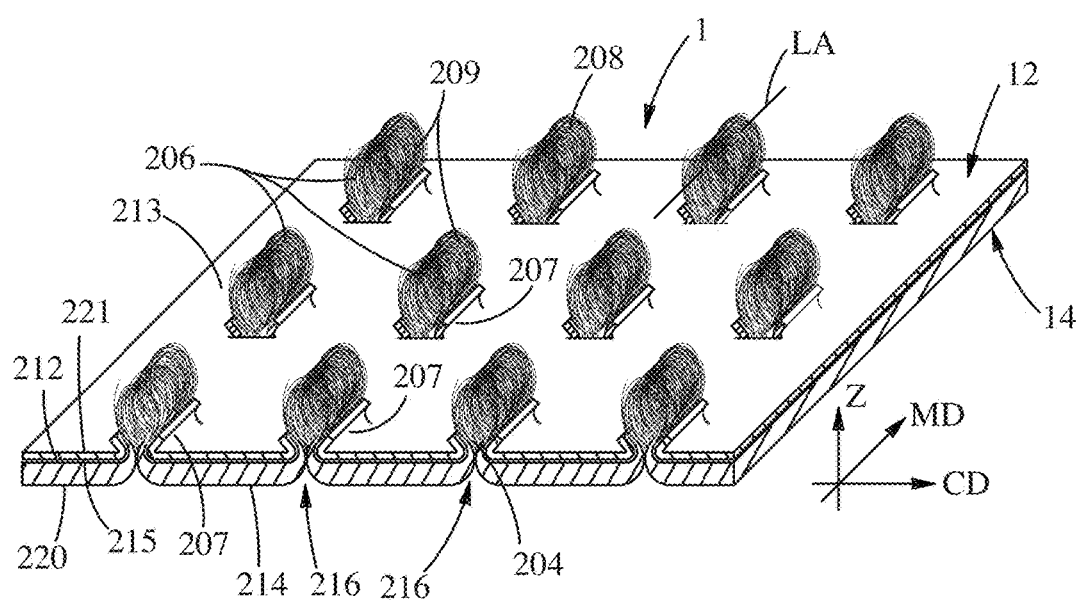
FIG. 25 is a schematic of a nonwoven having tufts.

An arrangement of tufted fibers 206 can be provided to substrates for use in a topsheet 20. A plurality of tufted fibers 206 can form a tuft 209. Tufts 209 can comprise a laminate web 1 comprised of two or more layers in which one of the layers is pushed into the other layer or protrudes through apertures in the other layer, an example of which is shown in FIG. 25. The layers are referred to herein as generally planar, two-dimensional precursor webs, such as first precursor web 220 and second precursor web 221. Either precursor web can be a film, a nonwoven, or a woven web. First precursor web 220 and second precursor web 221 (and any additional webs) can be joined with or without adhesive, thermal bonding, ultrasonic bonding and the like.

Web 1 has a first side 12 and a second side 14, the term "sides" being used in the common usage of generally planar two-dimensional webs, such as paper and films that have two sides when in a generally flat condition. First precursor web 220 has a first precursor web first surface 212 and a first precursor web second surface 214. Second precursor web 221 has a second precursor web first surface 213 and a second precursor web second surface 215. Web 1 has a machine direction (MD) and a cross machine direction (CD) as is commonly known in the art of web manufacture. The first precursor web 220 can be a nonwoven web comprised of substantially randomly oriented fibers, a polymer film, or a woven web. By "substantially randomly oriented" it is meant that, due to processing conditions of the precursor web, there may be a higher amount of fibers oriented in the MD than the CD, or vice-versa. Second precursor web 221 can be a nonwoven web similar to the first precursor web 220, or a polymer film or an apertured polymer film, such as a polyethylene film.

In one embodiment, first side 12 of web 1 is defined by exposed portions of the second precursor web first surface 213 and one or more tufts 209, which can be discrete tufts, which are integral extensions of the fibers of a nonwoven first precursor web 220. Tufts 209 can protrude through apertures in the second precursor web 221. As shown in FIG. 25, each tuft 209 can comprise a plurality of looped fibers 208 oriented out of the plane of the nonwoven. A tuft 209 can extend through second precursor web 221 and outwardly from the second precursor web first surface 213 thereof.

A textured region of tufts 209 can comprise a laminate web 1 comprising a first precursor web 220, at least the first precursor web 220 being a nonwoven web 130, the laminate web 1 having a first side 12, the first side 12 comprising the second precursor web 221 and at least one discrete tuft 209, each tuft 209 comprising a plurality of tufted fibers 206 being integral extensions of the first precursor web 220 and extend through the second precursor web 221, the laminate web 1 having a second side 14, the second side 14 comprising the first precursor web 220.

First precursor web 220 can be a fibrous woven or nonwoven web comprising elastic or elastomeric fibers. Elastic or elastomeric fibers can be stretched at least about 50% and return to within 10% of their original dimension. Tufts 209 can be formed from elastic fibers if the fibers are simply displaced due to the mobility of the fiber within the nonwoven, or if the fibers are stretched beyond their elastic limit and are plastically deformed.

Second precursor web 221 can be virtually any web material provided that the material has sufficient integrity to be formed into the laminate by the process described below, and that it has elongation properties relative to first precursor web 220, such that upon experiencing the strain of fibers from first precursor web 220 being urged out-of-plane in the direction of second precursor web 221, second precursor web 221 will be urged out of plane (e.g. by stretching) or rupture (e.g. by tearing due to extensional failure). If rupture occurs, IPS apertures 204 can be formed at the rupture locations (IPS stands for Inter-Penetrating Self). Portions of first precursor web 220 can extend through IPS apertures 204 (i.e., "push through" or protrude through) in second precursor web 221 to form tufts 209 on first side 12 of web 1. In one embodiment second precursor web 221 is a polymer film. Second precursor web 221 can also be a woven textile web, a nonwoven web, a polymer film, an apertured polymer film, a paper web, (e.g., tissue paper), a metal foil (e.g., aluminum wrapping foil), a foam (e.g., urethane foam sheeting), or the like.

As shown in FIG. 25, tufts 209 can extend through IPS apertures 204 in second precursor web 221. IPS apertures 204 can be formed by locally rupturing second precursor web 221. Rupture may involve a simple splitting open of second precursor web 221, such that IPS apertures 204 are in-plane (MD-CD) two-dimensional apertures. However, for some materials, such as polymer films, portions of second precursor web 221 can be deflected or urged out-of-plane (i.e., the plane of second precursor web 221) to form flap-like structures, referred to herein as a flap, or flaps, 207. The form and structure of flaps 207 can be dependent upon the material properties of second precursor web 221. Flaps 207 can have the general structure of one or more flaps, as shown in FIG. 25. In other embodiments, flap 207 can have a more volcano shaped structure, as if the tuft 209 is erupting from the flap 207.

Tufts 209 can be, in a sense, "pushed through" (or protrude through) second precursor web 221 and can be "locked" in place by frictional engagement with IPS apertures 204. This indicates a certain amount of recovery at the opening that tends to constrain tuft 209 from pulling back out through IPS apertures 204. The frictional engagement of the tufts and openings can provide for a laminate web structure having tufting on one side that can be formed without adhesives or thermal bonding.

Tufts 209 can be spaced sufficiently closely so as to substantially (for instance cover more than about 65%, about 75%, about 85%, or about 95% of the portion, zone, or region of interest) effectively cover first side 12 of web 1 when tufts 209 protrude through second precursor web 221. In such an embodiment, both sides of web 1 appear to be nonwoven, with a difference between first side 12 and second side 14 being a difference in surface texture. Therefore, in one embodiment, the web 1 can be described as a laminate material of two or more precursor webs, wherein both sides of the laminate web are substantially covered by fibers from only one of the precursor webs.

The looped fibers 208 can be substantially aligned with one another, as shown in FIG. 25. The looped fibers can be arranged such that tuft 209 has a distinct linear orientation and a long axis LA, as shown in FIG. 25. In the embodiment shown in FIG. 25, long axis LA is parallel to the MD. The tuft 209 can have a symmetrical shape in the MD-CD plane, such as a circular shape or square shape. Tufts 209 can have an aspect ratio (ratio of longest dimension to shortest dimension, both measured in the MD-CD plane) greater than 1. In one embodiment, all the spaced apart tufts 209 have generally parallel long axes LA. The number of tufts 209 per unit area of web 1, i.e., the area density of tufts 209, can be varied from about 1 tuft/cm$^2$ to about 100 tufts/cm$^2$. There can be at least about 10, or at least about 20 tufts/cm$^2$.

Figure 26:
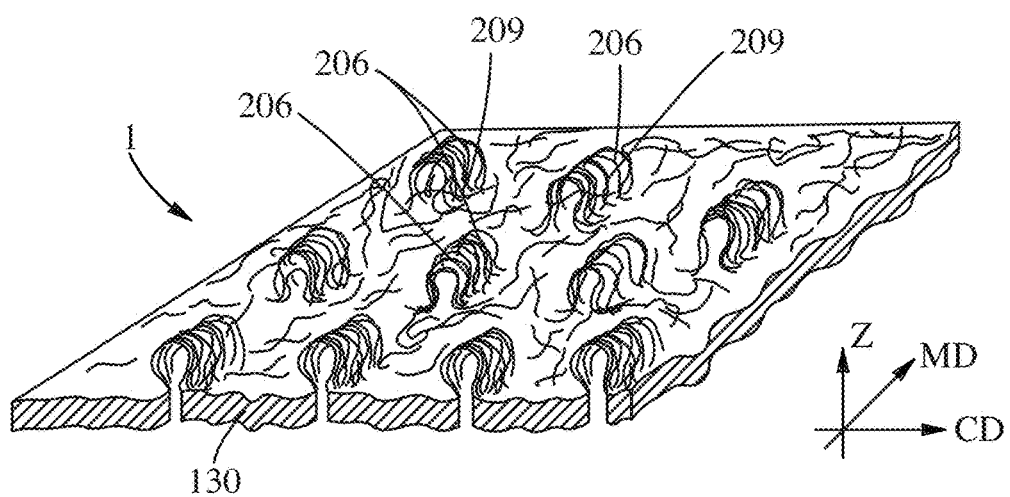
FIG. 26 is a schematic of a nonwoven having tufts.

Tufts 209 can be formed by urging fibers out-of-plane in the z-direction at discrete, localized, portions of first precursor web 220. Tufts 209 can be formed in the absence of second precursor web 221, as illustrated in FIG. 26, using the process as described below.

Figure 27:
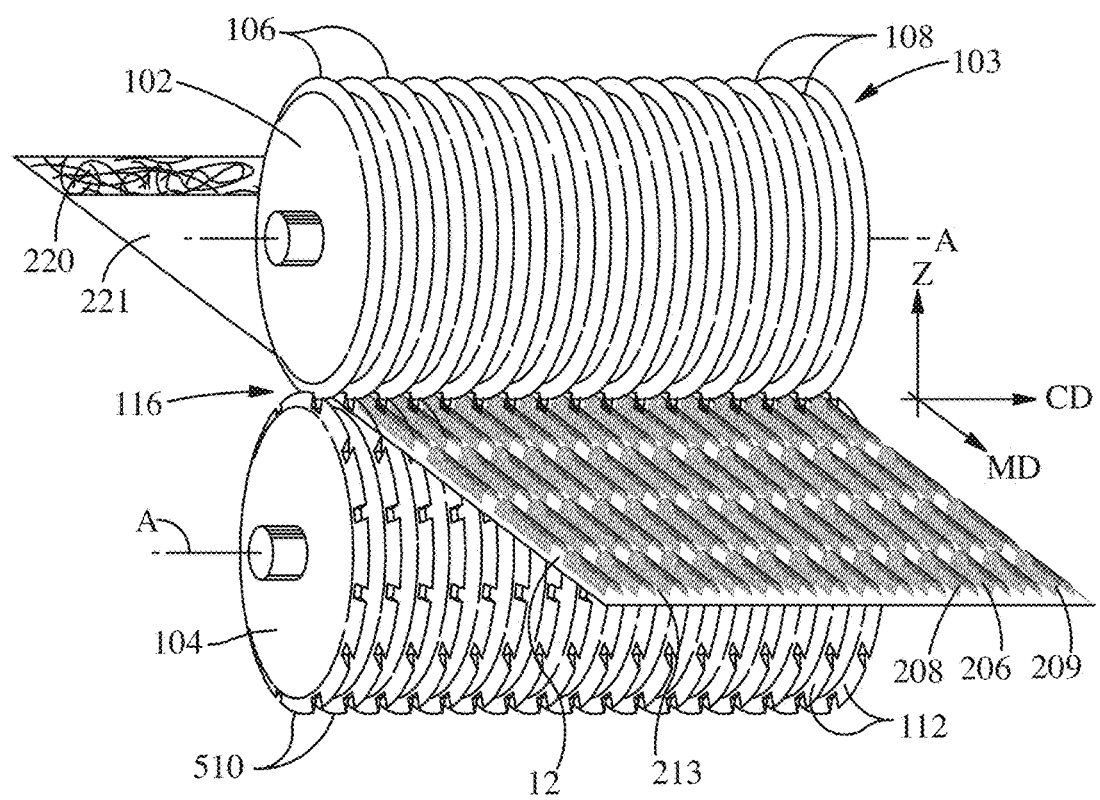
FIG. 27 is a schematic of a apparatus for forming tufts.

Referring to FIG. 27 there is shown an apparatus and method for making a web 1 comprising tufts 209 that can be used to form topsheet 20. The forming apparatus 103 comprises a pair of intermeshing rolls 102 and 104, each rotating about an axis A, the axes A being parallel in the same plane. Roll 102 comprises a plurality of ridges 106 and corresponding valleys 108 which can extend unbroken about the entire circumference of roll 102. Roll 104 can comprise a plurality of rows of circumferentially-extending ridges that have been modified to be rows of circumferentially-spaced teeth 510 that extend in spaced relationship about at least a portion of roll 104. Portions of roll 104 can be without teeth 510 to permit forming a web 1 having portions without tufts 209. Size and/or spacing of teeth 510 can be varied to permit formation of a web 1 having different size tufts 209 in different portions and/or have portions without tufts 209.

The individual rows of teeth 510 of roll 104 are separated by corresponding grooves 112. In operation, rolls 102 and 104 intermesh such that the ridges 106 of roll 102 extend into the grooves 112 of roll 104 and the teeth 510 of roll 104 extend into the valleys 108 of roll 102. Both or either of rolls 102 and 104 can be heated by means known in the art such as by using hot oil filled rollers or electrically-heated rollers.

In FIG. 27 the forming apparatus 103 is shown as having one patterned roll, e.g., roll 104, and one non-patterned grooved roll 102. Two patterned rolls 104 having either the same or differing patterns, in the same or different corresponding regions of the respective rolls can be used. An apparatus can be designed to have teeth pointing in opposite directions on opposing rolls. This can result in a web with tufts 209 being produced on both sides of the web.

Web 1 can be made by mechanically deforming precursor webs, such as first precursor web 220 and second precursor web 221, that can each be described as generally planar and two dimensional prior to processing by the apparatus shown in FIG. 27. By "planar" and "two dimensional" is meant simply that the webs start the process in a generally flat condition relative to the web 1 that has distinct, out-of-plane, z-direction three-dimensionality due to the formation of tufts 209.

The process and apparatus for forming tufts 209 is similar in many respects to a process described in U.S. Pat. No. 5,518,801 entitled "Web Materials Exhibiting Elastic-Like Behavior" and referred to in subsequent patent literature as "SELF" webs, which stands for "Structural Elastic-like Film". As described below, the teeth 510 of roll 104 have a geometry associated with the leading and trailing edges that permit the teeth to essentially "push" through the plane of the first precursor web 220 and second precursor web 221. In a two layer laminate web, the teeth 510 urge fibers from a first precursor web 220 simultaneously out-of-plane and through the plane of second precursor web 221. Therefore, tufts 209 of web 1 can be "tunnel-like" tufts of looped fibers 208 extending through and away from the second precursor web first surface 213 and can be symmetrically shaped.

First precursor web 220 and second precursor web 221 are provided either directly from their respective web making processes or indirectly from supply rolls and moved in the machine direction to the nip 116 of counter-rotating intermeshing rolls 102 and 104. The precursor webs are preferably held in a sufficient web tension so as to enter the nip 116 in a generally flattened condition by means well known in the art of web handling. As first precursor web 220 and second precursor web 221 pass through the nip 116, the teeth 510 of roll 104 which are intermeshed with valleys 108 of roll 102 simultaneously urge portions of first precursor web 220 out of the plane of first precursor web 220, and in some instances, through second precursor web 221 to form tufts 209. In effect, teeth 510 "push" fibers of first precursor web 220 into or through the plane of the second precursor web 221.

As the tip of teeth 510 push into or through first precursor web 220 and second precursor web 221, the portions of the fibers of first precursor web 220 that are oriented predominantly in the CD across teeth 510 are urged by the teeth 510 out of the plane of first precursor web 220. Fibers can be urged out of plane due to fiber mobility, or they can be urged out of plane by being stretched and/or plastically deformed in the z-direction. Portions of first precursor web 220 urged out of plane by teeth 510 push into or through second precursor web 221, which can rupture due to its relatively lower extensibility, thereby resulting in formation of tufts 209 on first side 12 of web 1.

For a given maximum strain (e.g., the strain imposed by teeth 510 of forming apparatus 103), second precursor web 221 can actually fail under the tensile loading produced by the imposed strain. That is, for the tufts 209 to be disposed on the first side 12 of web 1, second precursor web 221 may need to have sufficiently low fiber mobility (if any) and/or relatively low elongation-to-break such that it locally (i.e., in the area of strain) fails in tension, thereby producing IPS apertures 204 through which tufts 209 can extend.

In one embodiment, second precursor web 221 has an elongation to break in the range of about 1% to about 5%. While the actual required elongation to break depends on the strain to be induced to form web 1, it is recognized that in some embodiments, second precursor web 221 can exhibit a web elongation-to-break of about 6%, about 7%, about 8%, about 9%, about 10%, or more. It is also recognized that actual elongation-to-break can depend on the strain rate, which, for the apparatus shown in FIG. 27, is a function of line speed. Elongation to break of webs can be measured by means known in the art, such as by standard tensile testing methods using standard tensile testing apparatuses, such as those manufactured by Instron, MTS, Thwing-Albert, and the like.

Furthermore, relative to first precursor web 220, second precursor web 221 can have lower fiber mobility (if any) and/or lower elongation-to-break (i.e., elongation-to-break of individual fibers, or, if a film, elongation-to-break of the film) such that, rather than extending out-of-plane to the extent of the tufts 209, second precursor web 221 can fail in tension under the strain produced by the formation of tufts 209, e.g., by the teeth 510 of forming apparatus 103. In one embodiment, second precursor web 221 exhibits sufficiently low elongation-to-break relative to first precursor web 220 such that flaps 207 of IPS apertures 204 only extend slightly out-of-plane, if at all, relative to tufts 209. Second precursor web 221 can have an elongation to break of at least about 10% less than the first precursor web 220, or at least about 30% less, or at least about 50% less, or at least about 100% less than that of first precursor web 220.

The number, spacing, and size of tufts 209 can be varied by changing the number, spacing, and size of teeth 510 and making corresponding dimensional changes as necessary to roll 104 and/or roll 102.

A tufted web 1 can be formed from a nonwoven first precursor web 220 having a basis weight of between about 60 gsm and about 100 gsm (80 gsm being practical) and a polyolefinic film (e.g., polyethylene or polypropylene) second precursor web 221 having a density of about 0.91 to about 0.94 g/cm$^3$ and a basis weight of about 20 gsm.

Figure 28:
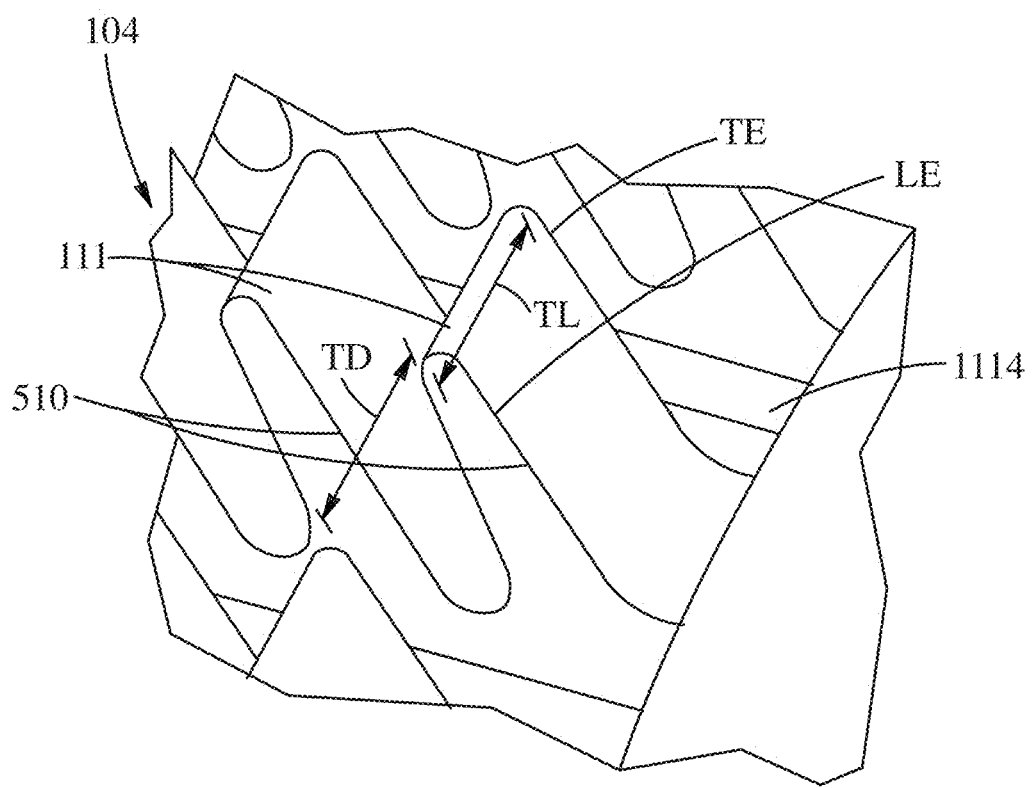
FIG. 28 is a schematic of teeth for forming tufts.

An enlarged view of teeth 510 is shown in FIG. 28. Teeth 510 can have a circumferential length dimension TL measured generally from the leading edge LE to the trailing edge TE at the tooth tip 111 of about 1.25 mm and can be uniformly spaced from one another circumferentially by a distance TD of about 1.5 mm. For making a web 1 from precursor web 24 having a total basis weight in the range of about 60 to about 100 gsm, teeth 510 of roll 104 can have a length TL ranging from about 0.5 mm to about 3 mm and a spacing TD from about 0.5 mm to about 3 mm, a tooth height TH ranging from about 0.5 mm to about 5 mm, and a pitch P between about 1 mm (0.040 inches) and about 5 mm (0.200 inches). Depth of engagement E can be from about 0.5 mm to about 5 mm (up to a maximum equal to tooth height TH). Of course, E, P, TH, TD and TL can be varied independently of each other to achieve a desired size, spacing, and area density of tufts 209.

The tooth tip 111 can be elongated and can have a generally longitudinal orientation, corresponding to a long axes LA of tufts 209 and discontinuities 216. It is believed that to get the tufted, looped tufts 209 of the web 1 that can be described as being terry cloth-like, the LE and TE should be very nearly orthogonal to the cylindrical surface 1114 of roll 104. As well, the transition from the tip 111 and LE or TE should be a sharp angle, such as a right angle, having a sufficiently small radius of curvature such that teeth 510 can push through second precursor web 221 at the LE and TE. Without being bound by theory, it is believed that having relatively sharply angled tip transitions between the tip of tooth 510 and the LE and TE permits the teeth 510 to push through first precursor web 220 and second precursor web 221 "cleanly", that is, locally and distinctly, so that the first side 12 of the resulting web 1 has tufts 209. When so processed, the web 1 may not be imparted with any particular elasticity, beyond what the first precursor web 220 and second precursor web 221 may have possessed originally. The pushing through of the second precursor web 221 can result in a small portion of the second precursor web 221 forming "confetti" or small pieces.

Web 1 having tufts 209 can be used as a topsheet 20 or a portion of topsheet 20 of absorbent article 10. Web 1 having tufts 209 can be beneficial as a topsheet 20 for absorbent articles due to the combination of excellent fluid acquisition and distribution to the absorbent core 40, and excellent prevention of rewet to the body-facing surface of topsheet 20 when in use. Rewet can be a result of at least two causes: (1) squeezing out of the absorbed fluid due to pressure on the absorbent article 10; and/or (2) wetness entrapped within or on the topsheet 20.

Surface texture in various portions of the topsheet 20 can be created by providing tufts 209. Tufts 209 can be oriented such that tufts 209 comprise a portion of the body facing surface 22 of the topsheet 20. Tufts 209 can be oriented such that tufts 209 are oriented on the garment facing surface of the topsheet 20.

U.S. Patent Publications US 20040131820 A1, filed on Dec. 16, 2003, in the name of Turner et al., US 20040265534 A1, filed on Dec. 16, 2003, in the name of Curro et al., US 20040265533 A1, filed on Dec. 16, 2003, in the name of Hoying et al., US 20040229008 A1, filed on Dec. 16, 2003, in the name of Hoying et al., US 20050281976 A1, filed Jun. 17, 2005, in the name of Curro et al., US 20050281976 A1, filed on Jun. 17, 2005, in the name of Curro et al. disclose are variety of structures forming tufts 209 and methods of making such tufts 209.

A topsheet 20 can be made by using a nonwoven first precursor web 220 and a fluid impermeable or fluid permeable polyethylene film second precursor web 221. The basis weights of the component webs can be varied, however, in general due to cost and benefit considerations a total basis weight of between about 20 gsm and about 80 gsm can be desirable for web 1. When made as a film/nonwoven laminate, web 1 can combine the softness and fluid capillarity of fiber tufts and the rewet prevention of a fluid impermeable polymer film.

Figure 5:
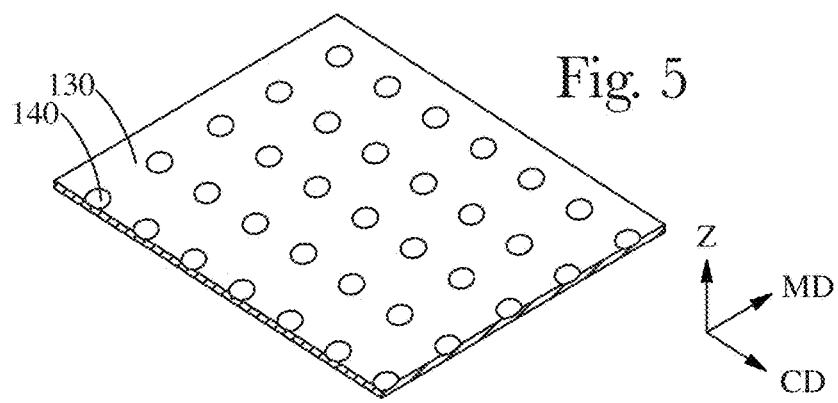
FIG. 5 is schematic of a nonwoven having embossments.

Embossments 140, as illustrated in FIG. 5, can be formed in the substrate comprising the topsheet 20 by passing the substrate between a smooth roller and an embossing roller having projections thereon. As the substrate passes between the smooth roller and embossing roller, thermoplastic fibers in the substrate are deformed and bonded together with one another and the fiber density of the nonwoven in the embossment 140 is greater than that for portions adjacent to the embossment 140.

In one embodiment, the absorbent core 40 can be between a laminate web comprising first precursor web 220 and second precursor web 221 such that neither the first precursor web 220 nor the second precursor web 221 or a portion of either the first precursor web 220 or second precursor web 221 is between the absorbent core 40 and the backsheet 30.

Texture can be measured using a GFM Mikrocad Optical Profiler instrument commercially available from GFMesstechnik GmbH, Warthestraße 21, D14513 Teltow/Berlin, Germany. The GFM Mikrocad Optical Profiler instrument includes a compact optical measuring sensor based on the digital micro mirror projection, consisting of the following main components: a) DMD projector with 1024×768 direct digital controlled micro mirrors, b) CCD camera with high resolution (1300×1000 pixels), c) projection optics adapted to a measuring area of at least 40 mm×40 mm down to 4 mm×3 mm, and d) matching resolution recording optics; a table tripod based on a small hard stone plate; a cold light source; a measuring, control, and evaluation computer; measuring, control, and evaluation software ODSCAD 4.0, English version; and adjusting probes for lateral (x-y) and vertical (z) calibration.

The GFM Mikrocad Optical Profiler system measures the surface height of a sample using the digital micro-mirror pattern projection technique. The result of the analysis is a map of surface height (z) vs. xy displacement. The system has a field of view of 27×22 mm with a resolution of 21 microns. The height resolution should be set to between 0.10 and 1.00 micron. The height range is 64,000 times the resolution.

To measure the texture of a material or composite material the following can be performed: (1) Turn on the cold light source. The settings on the cold light source should be 4 and C, which should give a reading of 3000K on the display; (2) Turn on the computer, monitor and printer and open the ODSCAD 4.0 or higher Mikrocad Software; (3) Select "Measurement" icon from the Mikrocad taskbar and then click the "Live Pic" button; (4) Place a 5 mm by 5 mm sample of fibrous structure product conditioned at a temperature of 73° F.±2° F. (about 23° C.±1° C.) and a relative humidity of 50%±2% under the projection head and adjust the distance for best focus; (5) Click the "Pattern" button repeatedly to project one of several focusing patterns to aid in achieving the best focus (the software cross hair should align with the projected cross hair when optimal focus is achieved). Position the projection head to be normal to the sample surface; (6) Adjust image brightness by changing the aperture on the camera lens and/or altering the camera "gain" setting on the screen. Set the gain to the lowest practical level while maintaining optimum brightness so as to limit the amount of electronic noise. When the illumination is optimum, the red circle at bottom of the screen labeled "I.O." will turn green; (7) Select Standard measurement type; (8) Click on the "Measure" button. This will freeze the live image on the screen and, simultaneously, the surface capture process will begin. It is important to keep the sample still during this time to avoid blurring of the captured images. The full digitized surface data set will be captured in approximately 20 seconds; (9) If the surface data is satisfactory, save the data to a computer file with ".omc" extension. This will also save the camera image file ".kam"; (10) To move the surface data into the analysis portion of the software, click on the clipboard/man icon; (11) Now, click on the icon "Draw Lines". Draw a line through the center of a region of features defining the texture of interest. Click on Show Sectional Line icon. In the sectional plot, click on any two points of interest, for example, a peak and the baseline, then click on vertical distance tool to measure height in microns or click on adjacent peaks and use the horizontal distance tool to determine in-plane direction spacing; and (12) for height measurements, use 3 lines, with at least 5 measurements per line, discarding the high and low values for each line, and determining the mean of the remaining 9 values. Also record the standard deviation, maximum, and minimum. For x and/or y direction measurements, determine the mean of 7 measurements. Also record the standard deviation, maximum, and minimum. Criteria that can be used to characterize and distinguish texture include, but are not limited to, occluded area (i.e. area of features), open area (area absent of features), spacing, in-plane size, and height. If the probability that the difference between the two means of texture characterization is caused by chance is less than 10%, the textures can be considered to differ from one another.

Textures can also be compared to and distinguished from one another visually by an ordinary observer having 20/20 vision from a distance of 30 cm in lighting at least equal to the illumination of a standard 100 watt incandescent white light bulb. If the ordinary observer can distinguish between the textures, the textures can be considered to differ from one another.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a. a topsheet comprising:
      i. a central region consisting of a combination of a apertured film and a nonwoven;
      ii. an intermediate and/or edge region that is laterally outward from said central region, said intermediate and/or edge region consisting of the apertured film;
      iii. wherein said nonwoven comprises apertures; and
      iv. wherein said apertured film and said nonwoven do not completely overlap with one another; and
   b. an absorbent core in facing relationship with said topsheet.

2. The absorbent article of claim 1, wherein said topsheet further comprises a plurality of fiber tufts disposed in said intermediate region.

* * * * *